(12) United States Patent
Skelton et al.

(10) Patent No.: US 9,937,342 B2
(45) Date of Patent: Apr. 10, 2018

(54) SHIFTING OF ELECTRICAL STIMULATION ELECTRODE COMBINATIONS AMONG DIFFERENTLY SIZED ELECTRODE ARRAYS

(75) Inventors: Dennis M. Skelton, Minneapolis, MN (US); Joseph J. Nolan, Minnetonka, MN (US); Nathan A. Torgerson, Andover, MN (US); Wende L. Dewing, Edina, MN (US); Todd V. Smith, Shoreview, MN (US); Shyam Gokaldas, Minneapolis, MN (US); Steven M. Goetz, North Oaks, MN (US); Andrew H. Houchins, Lino Lakes, MN (US); Jeffrey T. Keacher, Stanford, CA (US)

(73) Assignee: Medtronic, Inc., Minneapolis, MN (US)

( * ) Notice: Subject to any disclaimer, the term of this patent is extended or adjusted under 35 U.S.C. 154(b) by 1917 days.

(21) Appl. No.: 12/110,906

(22) Filed: Apr. 28, 2008

(65) Prior Publication Data
US 2009/0018619 A1     Jan. 15, 2009

Related U.S. Application Data

(60) Provisional application No. 60/926,926, filed on Apr. 30, 2007.

(51) Int. Cl.
*A61N 1/05* (2006.01)
*A61N 1/372* (2006.01)

(52) U.S. Cl.
CPC ....... *A61N 1/0553* (2013.01); *A61N 1/37247* (2013.01); *A61N 1/0531* (2013.01); *A61N 1/0534* (2013.01)

(58) Field of Classification Search
CPC .............. A61N 1/0553; A61N 1/37247; A61N 1/0531; A61N 1/0534
(Continued)

(56) References Cited

U.S. PATENT DOCUMENTS 3,025,857 A    3/1962  Browner
5,417,719 A *  5/1995  Hull et al. ...................... 607/46
(Continued)

FOREIGN PATENT DOCUMENTS

| WO | WO 2004/041353 | 5/2004 |
| WO | WO 2004/052446 | 6/2004 |
| WO | WO 2006/110690 | 10/2006 |

OTHER PUBLICATIONS

Skelton et al., "Parameter-Directed Shifting of Electrical Stimulation Electrode Combinations," U.S. Appl. No. 12/110,843, filed Apr. 28, 2008.
(Continued)

*Primary Examiner* — Michael Carey
*Assistant Examiner* — Roland Dinga
(74) *Attorney, Agent, or Firm* — Shumaker & Sieffert, P.A.

(57) ABSTRACT

The disclosure provides techniques for parameter-directed shifting of electrical stimulation electrode combinations. An external programmer permits a user to shift electrode combinations, e.g., along the length of a lead or leads. The external programmer accepts shift input and causes an electrical stimulator to shift electrode combinations as indicated by the input. Different sets of electrodes may have different electrode counts. For example, an array of electrodes carried by one lead may have a greater number of electrodes than an array of electrodes carried on another lead. The disclosure provides techniques for shifting electrode combinations among leads with different electrode counts. For example, an external programmer may execute shifts in a series of shift operations, where the number of shift operations along the length of a lead having a greater electrode count is greater than the number of shift steps along the length of a lead having a lesser electrode count.

60 Claims, 21 Drawing Sheets

(58) Field of Classification Search
USPC .................................................. 607/2, 46, 54
See application file for complete search history.

(56) References Cited

U.S. PATENT DOCUMENTS

| | | | |
|---|---|---|---|
| 5,443,486 A | | 8/1995 | Hrdlicka et al. |
| 5,643,330 A | * | 7/1997 | Holsheimer et al. ........... 607/46 |
| 5,895,416 A | * | 4/1999 | Barreras et al. ................ 607/62 |
| 5,938,690 A | * | 8/1999 | Law et al. ...................... 607/46 |
| 6,052,624 A | | 4/2000 | Mann |
| 6,169,924 B1 | * | 1/2001 | Meloy et al. ................... 607/39 |
| 6,236,892 B1 | * | 5/2001 | Feler .............................. 607/117 |
| 6,516,227 B1 | | 2/2003 | Meadows et al. |
| 6,609,032 B1 | | 8/2003 | Woods et al. |
| 6,754,539 B1 | * | 6/2004 | Erickson et al. ............. 607/117 |
| 6,993,384 B2 | * | 1/2006 | Bradley et al. ................... 607/2 |
| 7,107,102 B2 | | 9/2006 | Daignault, Jr. et al. |
| 7,127,298 B1 | * | 10/2006 | He et al. ......................... 607/48 |
| 7,366,571 B2 | * | 4/2008 | Armstrong ...................... 607/45 |
| 2004/0034394 A1 | * | 2/2004 | Woods et al. ................... 607/46 |
| 2004/0267330 A1 | * | 12/2004 | Lee et al. ........................ 607/48 |
| 2005/0060007 A1 | * | 3/2005 | Goetz .............................. 607/48 |
| 2006/0229687 A1 | | 10/2006 | Goetz et al. |
| 2006/0241753 A1 | * | 10/2006 | Suaning et al. ............. 623/6.63 |
| 2006/0259099 A1 | | 11/2006 | Goetz et al. |
| 2007/0027514 A1 | | 2/2007 | Gerber |
| 2007/0203544 A1 | | 8/2007 | Goetz et al. |
| 2007/0255343 A1 | * | 11/2007 | McMahon et al. ............. 607/54 |

OTHER PUBLICATIONS

Skelton et al., "Parameter-Directed Shifting of Electrical Stimulation Electrode Combinations," U.S. Appl. No. 60/926,903, filed Apr. 30, 2007.
Product Manual, "Physician Implant Manual," for Implantable Pulse Generator Model SC1100, by Advanced Bionics, 2004 (31 pgs.).
Product Manual, "Patient System Handbook," for Precision Spinal Cord Stimulation System, by Advanced Bionics, 2004 (88 pgs.).
"Notification of Transmittal of the International Search Report and the Written Opinion of the International Searching Authority, or the Declaration" dated Jul. 31, 2008 for corresponding PCT Application No. PCT/US2008/005479 (12 pgs.).
Reply to Written Opinion dated Feb. 26, 2009 for corresponding PCT Application No. PCT/US2008/005479 (22 pgs.).
Notification of Transmittal of the International Preliminary Report on Patentability for corresponding patent Application No. PCT/US2008/005479, dated Jun. 16, 2009, 15 pgs.
Final office action for U.S. Appl. No. 12/110,843, dated Jul. 6, 2012, 10 pages.
Office action for U.S. Appl. No. 12/110,843, dated Dec. 6, 2012, 11 pages.
Response to office action for U.S. Appl. No. 12/110,843, filed Mar. 1, 2013, 11 pages.
Office Action for U.S. Appl. No. 12/110,843, dated Feb. 1, 2012, 11 pages.
Advisory action for U.S. Appl. No. 12/110,843, dated Oct. 26, 2012, 3 pages.
Response to office action for U.S. Appl. No. 12/110,843, filed Nov. 2, 2012, 27 pages.
Response to office action for U.S. Appl. No. 12/110,843, filed Jun. 11, 2013, 23 pages.
Office action for U.S. Appl. No. 12/110,843, dated Apr. 11, 2013, 10 pages.
Response to Office Action for U.S. Appl. No. 12/110,843, filed Apr. 27, 2012, 25 pages.
Response to final office action for U.S. Appl. No. 12/110,843, filed Sep. 27, 2012, 25 pages.
Examiner's Answer for U.S. Appl. No. 12/110,843, dated Nov. 6, 2013, 7 pages.
Reply Brief in Response to Examiner's Answer dated Jan. 6, 2014, from U.S. Appl. No. 12/110,843, filed Apr. 28, 2008, 8 pages.
Decision on Appeal from U.S. Appl. No. 12/110,843, dated Jun. 30, 2016, 13 pp.

* cited by examiner

SHIFTING OF ELECTRICAL STIMULATION ELECTRODE COMBINATIONS AMONG DIFFERENTLY SIZED ELECTRODE ARRAYS

RELATED APPLICATION

This application claims the benefit of U.S. Provisional Application No. 60/926,926, filed on Apr. 30, 2007, the entire contents of which is incorporated herein by reference.

TECHNICAL FIELD

The invention relates to electrical stimulation therapy and, more particularly, to selection of electrode combinations for delivery of electrical stimulation therapy to a patient.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. An implantable medical device may deliver electrical stimulation therapy via leads that include electrodes located proximate to the spinal cord, pelvic nerves, stomach, peripheral nerves, or within the brain of a patient. In general, the implantable medical device delivers electrical stimulation therapy in the form of electrical pulses or another electrical waveform.

A clinician selects values for a number of programmable parameters in order to define the electrical stimulation therapy to be delivered to a patient. For example, the clinician selects an amplitude, which may be a current or voltage amplitude, and, when electrical stimulation is delivered in the form of pulses, a pulse width for a stimulation waveform to be delivered to the patient, as well as a rate at which the pulses are to be delivered to the patient. The clinician may also select particular electrodes within an electrode set to be used as an electrode combination to deliver the electrical stimulation and the polarities of the selected electrodes. A set of parameter values may be referred to as a program in the sense that they drive the electrical stimulation therapy to be delivered to the patient.

Electrical stimulation may be delivered via electrodes carried by one, two or more implantable leads, each of which may include multiple electrodes. Electrical stimulation may be delivered via various combinations of electrodes, including electrodes on a single lead, or electrodes on different leads. For example, one program may specify a combination of relatively proximal electrodes while another program may specify a combination of more distal electrodes. In addition, some programs may include greater or lesser numbers of electrodes, greater or lesser distances between electrodes, or varied positions of cathodes and anodes. In this manner, electrical stimulation can be shaped and targeted relative to nerves, muscle or other tissue or anatomical structures to enhance therapeutic efficacy.

SUMMARY

In general, the disclosure provides techniques for parameter-directed shifting of electrical stimulation among different electrode combinations that may have substantially similar electrode patterns. Electrical stimulation may comprise voltage-based or current-based stimulation in various embodiments. An electrode combination is a selected subset of one or more electrodes. The electrodes may be located on one or more leads, such as implantable leads, coupled to an electrical stimulator. The electrode combination also may define the polarities of the electrodes in the selected subset. In accordance with this disclosure, an external programmer permits a user to shift electrical stimulation among different electrode combinations, e.g., along the length of a lead or leads. In particular, the external programmer accepts parameter-directed shift input and causes an electrical stimulator to shift electrode combinations as indicated by the input.

The external programmer may present an electrode combination as a parameter that can be adjusted to shift the electrode combination used to deliver a pattern of electrical stimulation, e.g., along the length of the lead. In some embodiments, for example, an electrode combination may be presented as an alphanumeric value that can be incremented, decremented, selected, or otherwise adjusted by a user to indicate a shift of an electrode combination in a desired direction, e.g., along the length of a lead or leads. In response, the external programmer may transmit one or more commands to an electrical stimulator to shift electrical stimulation from one electrode combination to another electrode combination, or among multiple electrode combinations. These various electrode combinations may each have electrode patterns that are substantially similar.

Different activities and positions encountered by a patient may result in different degrees of therapeutic efficacy, e.g., due to movement of electrodes relative to target sites. An external programmer that permits a patient or other user to shift electrode combinations in a manner similar to adjustments of other parameters may enable the patient to maintain or improve therapeutic efficacy. For example, shifting an electrode combination more proximally or more distally along the length of a set of leads may more effectively direct electrical stimulation energy to a target site, providing greater efficacy in treating diseases or disorders.

In some cases, different sets of electrodes may have different electrode counts. For example, an array of electrodes carried by one lead may have a greater number of electrodes than an array of electrodes carried on another lead. As an example, some leads may have four electrodes while other leads may have eight or sixteen electrodes. In some embodiments, the disclosure provides techniques for shifting electrode combinations among leads with different electrode counts. For example, an external programmer may execute shifts in steps, where the number of shift steps along the length of a lead having a greater electrode count is greater than the number of shift steps along the length of a lead having a lesser electrode count.

The electrical stimulator may shift between different electrode combinations gradually. For example, the electrical stimulator may ramp down the stimulation energy delivered via a first electrode combination and then ramp up the stimulation energy delivered via a second electrode combination. As another example, the electrical stimulator may shift from a first electrode combination to a second combination in a series of incremental steps such that electrical stimulation is delivered to both the first and second electrode combinations on a time-interleaved basis.

In one embodiment, the disclosure provides a method comprising causing an electrical stimulator to select a first electrode combination which, when active, delivers electrical stimulation to a patient, receiving user input indicating a parameter adjustment that indicates a shift to a second electrode combination having an electrode pattern that is substantially similar to that of the first electrode combination, and causing the electrical stimulator to select the second electrode combination in response to the user input.

In another embodiment, the disclosure provides an external programmer for an electrical stimulator, the programmer comprising a processor that generates a command to cause an electrical stimulator to select a first electrode combination, and a user interface that receives user input indicating a parameter adjustment that indicates a shift to a second electrode combination having an electrode pattern that is substantially similar to that of the first electrode combination, wherein the processor generates a command to cause the electrical stimulator to select the second electrode combination in response to the user input.

In an additional embodiment, the disclosure provides an electrical stimulator system comprising an electrical stimulator that delivers electrical stimulation via combinations of electrodes carried by one or more implantable leads, and an external programmer comprising a processor that generates a command to cause an electrical stimulator to select a first electrode combination, and a user interface that receives user input indicating a parameter adjustment that indicates a shift to a second electrode combination having an electrode pattern that is substantially similar to that of the first electrode combination, wherein the processor generates a command to cause the electrical stimulator to select the second electrode combination in response to the user input.

In another embodiment, the disclosure provides a method comprising delivering electrical stimulation via an electrode combination comprising an electrode in a first array and an electrode in a second array, wherein the second array includes a greater number of electrodes than the first array, and shifting the electrical stimulation to different electrode combinations in a series of shift operations, wherein one of the shift operations includes shifting the electrode in the second array while maintaining the electrode in the first array. In certain cases, the electrode combination further comprises an electrode in a third array, wherein the third array and the first array include a common number of electrodes, and wherein one of the shift operations includes shifting the electrode in the second array while maintaining the electrode in the first array and maintaining the electrode in the third array.

In a further embodiment, the disclosure provides an electrical stimulation device comprising a first array of electrodes, a second array of electrodes including a greater number of electrodes than the first electrode array, an electrical stimulation generator that generates electrical stimulation and delivers the electrical stimulation via an electrode combination comprising an electrode in the first array and an electrode in a second array, and a processor that controls the electrical stimulation generator to shift the electrical stimulation to different electrode combinations in a series of shift operations, wherein one of the shift operations includes shifting the electrode in the second array while maintaining the electrode in the first array. In certain cases, the device further comprises a third array of electrodes, wherein the third array and the first array include a common number of electrodes, wherein the electrode combination further comprises an electrode in the third array, and wherein one of the shift operations includes shifting the electrode in the second array while maintaining the electrode in the first array and maintaining the electrode in the third array.

In an additional embodiment, the disclosure provides an electrical stimulator system comprising an electrical stimulator that delivers electrical stimulation via an electrode combination comprising an electrode in a first array of electrodes and an electrode in a second array of electrodes, wherein the second array includes a greater number of electrodes than the first array, and an external programmer that controls the electrical stimulator to shift the electrical stimulation to different electrode combinations in a series of shift operations, wherein one of the shift operations includes shifting the electrode in the second array while maintaining the electrode in the first array. In certain cases, the electrode combination further comprises an electrode in a third array, wherein the third array and the first array include a common number of electrodes, and wherein one of the shift operations includes shifting the electrode in the second array while maintaining the electrode in the first array and maintaining the electrode in the third array.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
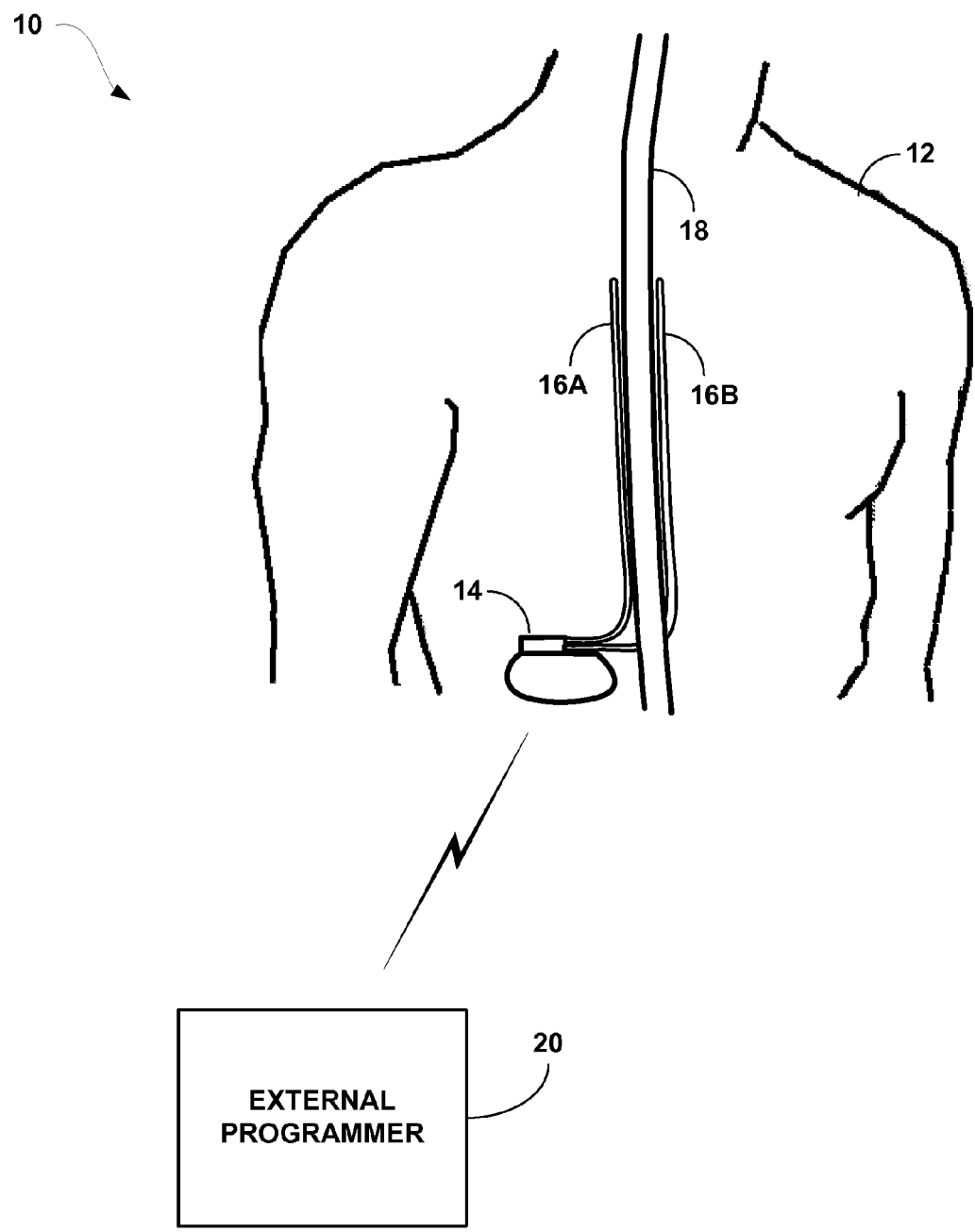
FIG. 1A is a schematic diagram illustrating an implantable stimulation system including a pair of implantable stimulation leads.

In general, the disclosure provides techniques for parameter-directed shifting of electrical stimulation electrode combinations. Electrical stimulation may comprise voltage-based or current-based stimulation in various embodiments. An electrode combination is a selected subset of one or more electrodes located on one or more leads, such as implantable leads, coupled to an electrical stimulator. Although electrodes deployed on leads will be described for purposes of illustration, the techniques described in this disclosure also may be applicable to arrays of electrodes arranged on leadless stimulators, e.g., as surface electrodes on or protrusions from a device housing. The electrodes may be arranged in rows and/or columns (or other patterns), where a row or column may form an electrode array. As a further alternative, the electrodes may be arranged in rows and/or columns on paddle leads. A paddle lead may carry a two-dimensional array of electrodes arranged in rows and columns. Each row or column may form an electrode array as described in this disclosure. The electrode combination also may specify the polarities of the electrodes in the selected subset. In accordance with this disclosure, an external programmer permits a user to shift electrode combinations along the length of a lead or leads. In particular, the external programmer accepts parameter-directed shift input and causes an electrical stimulator to shift electrode combinations as indicated by the input. In some embodiments, these electrode combinations each have a substantially similar electrode pattern. In some embodiments, the electrode combinations have a common number of electrodes.

The external programmer may present an electrode combination as a parameter that can be adjusted to shift the electrode combination along the length of the lead. As examples, a parameter adjustment may be a change in parameter value, e.g., by increment or decrement, or selection of a parameter value, each of which will be generally referred to as an adjustment. The parameter value may indicate an electrode combination or a shift from a first electrode combination to a second electrode combination (which may have an electrode pattern that is substantially similar to that of the first electrode combination), but may not directly indicate a position of the second electrode combination or a direction of the shift. In some embodiments, for example, an electrode combination may be presented as an alphanumeric value that can be incremented, decremented, or otherwise adjusted by a user, to indicate a shift of an electrode combination to another electrode combination in a desired direction along the length of a lead or leads. In response, the external programmer may transmit one or more commands to an electrical stimulator to shift electrode combinations.

Different activities and positions encountered by a patient may result in different degrees of therapeutic efficacy, e.g., due to movement of electrodes relative to target sites. For example, changes in posture, position or activity level may result in small changes in the positions of implanted leads relative to target stimulation sites. These changes in electrode position may be referred to as lead migration. Due to lead migration, the efficacy of therapy delivered via a particular electrode combination may vary acutely such that selection of a different electrode combination may be desirable. Also, longer term accommodation may result in more steady state reductions in therapeutic efficacy.

An external programmer may permit a patient to adjust stimulation parameters such as amplitude level in an attempt to maintain stimulation efficacy when lead migration occurs. In accordance with this disclosure, however, an external programmer further permits a patient or other user to shift electrode combinations in a manner similar to adjustments of other parameters. Shifting an electrode combination more proximally or more distally along the length of a set of leads may more effectively direct electrical stimulation energy to a target site, providing greater efficacy in treating diseases or disorders. Proximal generally refers to an end of the lead closer to an implantable pulse generator, while distal generally refers to an end further away from the implantable pulse generator.

Adjustment of a parameter to shift electrode combinations may be referred to as parameter-directed shifting. Parameter-directed shifting of electrode combinations may present a simple interface that enables the patient to quickly shift electrode combinations to maintain or improve therapeutic efficacy, particularly in the event lead migration undermines efficacy. By selecting different electrode combinations via a parameter adjustment, a user can shift electrode combinations in a manner similar to other parameter adjustments to which the user may be accustomed, such as group selection, program selection, amplitude adjustments, pulse width adjustment or pulse rate adjustment.

In some cases, a set of leads may include leads with different electrode counts. As an example, some leads may have four electrodes while other leads may have eight or sixteen electrodes. In some embodiments, the disclosure provides techniques for shifting electrode combinations among leads with different electrode counts. In particular, an external programmer may execute shifts in steps, where the number of shift steps along the length of a lead having a greater electrode count is greater than the number of shift steps along the length of a lead having a lesser electrode count. If a first lead carries four electrodes and a second lead carries eight electrodes, for example, parameter adjustments may direct a shift of one electrode level on the first lead for every two electrode levels on the second lead. The electrical stimulator may shift between different electrode combinations gradually.

For example, the electrical stimulator may ramp down the stimulation energy delivered via a first electrode combination to cause termination of delivery of electrical stimulation via the first electrode combination, and then ramp up the stimulation energy delivered via a second electrode combination to cause initiation of delivery of electrical stimulation via the second electrode combination following termination of delivery of electrical stimulation via the first electrode combination. As another example, the electrical stimulator may shift from a first electrode combination to a second combination in a series of incremental steps such that electrical stimulation is delivered to both the first and second electrode combinations on a time-interleaved basis. For example, the electrical stimulator may include a single stimulation pulse generator that is capable of generating pulses or waveforms according to two or more different programs on an alternating basis, and a switch device configured to switch the electrical stimulation across different electrode combinations on an alternating basis. In this manner, stimulation can be ramped down for a first electrode combination in first time slots, while stimulation is ramped up for a second electrode combination in second time slots.

In general, the electrical stimulator may be an implantable stimulator or an external stimulator. In addition, the electrical stimulator may be a chronic stimulator intended for use over an extended period of time on the order of months or years. Alternatively, the electrical stimulator may be a trial stimulator intended for use over a shorter period on the order of days, weeks or months. The stimulator may deliver electrical stimulation therapy via one or more implantable leads that include electrodes for location proximate to target locations associated with the spinal cord, peripheral nerves, pelvic nerves, gastric nerves, or brain.

Stimulation may be used in different therapeutic applications, such as spinal cord stimulation (SCS), e.g., for pain, deep brain stimulation (DBS), cortical stimulation (CS), peripheral nerve stimulation (PNS), pelvic floor stimulation, gastric stimulation, and peripheral nerve field stimulation (PNFS). Stimulation may be configured to support therapy for a variety of symptoms, diseases and disorders, such as chronic pain, temporary pain, urinary incontinence, fecal incontinence, sexual dysfunction, gastroparesis, obesity, movement disorders, epilepsy, depression, anxiety, or the like.

In this disclosure, the techniques for parameter-directed shifting of electrode combinations will be described in the context of electrical spinal cord stimulation therapy for pain management for purposes of illustration, but without limitation as to application of such techniques to other target sites or therapy applications.

Chronic pain may be a debilitating condition for a patient. Pain may prevent the patient from performing certain activities, interacting with other people in social situations, or even sleeping regularly. Chronic pain may be the result of injury, disease, age, or other conditions. Pain may originate at organs, muscles, nerves, or other tissues, and most pain signals are transferred through the spinal cord. Electrical stimulation of certain nerves, nerve plexuses, or the spinal cord may provide an effective therapy for pain experienced by the patient. Stimulation of the brain may also be effective for alleviating pain, such as neuropathic or nociceptive pain. Stimulation of nerves, nerve plexuses, the spinal cord, and the brain may be referred to as neurostimulation or neuromodulation.

In some embodiments of this disclosure, an implantable electrical stimulator may be provided. The electrical stimulator may be a stimulator that delivers electrical stimulation to, for example, a portion of the spinal cord to block pain signals being transferred to the brain of the patient. In some cases, electrical stimulation may permanently reduce chronic pain. However, stimulation with the same stimulation parameter set may become less efficacious through time due to accommodation. In other cases, temporary or permanent lead migration may result in reduced therapeutic efficacy for a given set of stimulation parameters, which may include stimulation current or voltage amplitude and electrode combination and, in the case of electrical stimulation delivered in the form of pulses, pulse width and pulse rate. In general, an electrode combination defines a selected set of electrodes on one lead or across multiple leads, as well as the polarities of the individual electrodes, and hence the formation of cathodes and anodes with the set of electrodes. Although primarily described herein with reference to stimulation delivered as pulses, embodiments of the invention may deliver or control delivery of stimulation in the form of continuous time signals or other types of waveforms.

An external programmer that accepts parameter-directed user input to indicate shifting of electrode combinations may provide a quick and simple interface that permits a patient or other user to change electrode combinations in an effort to maintain or improve therapeutic efficacy. The shifting of electrode combinations may be made to address acute reductions in efficacy due to posture, position or activity, and associated lead migration. As an illustration, if a patient bends over during the course of exercise, it is possible that the selected electrode combination may be slightly displaced relative to a target site, resulting in a reduced or less reliable transfer of stimulation energy. Alternatively, the shifting of electrode combinations may be responsive to more long term reductions in efficacy, e.g., due to accommodation.

A parameter-directed technique for shifting of electrode combinations can assist a patient or other user in dynamically making electrode combination adjustments in response to perceived efficacy. The electrode shifting capability can be presented in a manner similar to adjustments of other parameters, providing a simplified interface that may require little additional training or experience. To facilitate parameter-directed shifting, a physician may define one or more shiftable groups on a program-by-program basis and communicate the shiftable group information for storage in the memory of the stimulator. In other examples, the shiftable group information may be stored in a patient programmer in addition to or in place of the stimulator. A group may refer to a group of programs that may be delivered simultaneously or on an interleaved basis. A program refers to a set of stimulation parameters, which may include amplitude, pulse width, pulse rate, and electrode combination. Again, an electrode combination may indicate selected electrodes and associated polarities for delivery of stimulation therapy.

For a current group, the external programmer may present parameters such as amplitude, pulse width and pulse rate for each of the programs in the group. To adjust parameters for a given program, the user may select the program from the group and then adjust selected parameters as desired. The external programmer may also permit a user to select different groups of programs. If a currently selected program is designated as shiftable, the external programmer may allow a patient or other user to access the shift feature as if it were another parameter. This feature may be especially convenient for patients, but may benefit other users such as physicians or other caregivers.

By adjusting the shift parameter, the user can shift from the current electrode combination to another electrode combination for the delivery of stimulation according to the currently selected program. Electrode combinations or shifts can be represented by alphanumeric parameter values, similar to other parameters. In particular, each of a plurality of alphanumeric characters may indicate a shift to one of a plurality of electrode combinations. In some cases, the electrode combination parameter values may be increased or decreased, e.g., using increase or decrease keys, similar to adjustment of other parameter values like amplitude, pulse width or pulse rate. In this manner, the programmer interface may provide a simple, convenient and user-friendly technique for shifting electrode combinations, particularly for patients.

FIG. 1A is a schematic diagram illustrating an implantable stimulation system 10 including a pair of implantable electrode arrays in the form of stimulation leads. As shown in FIG. 1A, system 10 includes an implantable stimulator 14 and external programmer 20 shown in conjunction with a patient 12. Although FIG. 1A shows implantable stimulator 14, the parameter-directed shifting techniques described in this disclosure may be applied to external stimulators. Stimulation energy is delivered from stimulator 14 to spinal cord 18 of patient 12 via one or more electrodes of implantable leads 16A and 16B (collectively "leads 16"). In some applications, such as spinal cord stimulation (SCS), the adjacent implantable leads 16 may have longitudinal axes that are substantially parallel to one another.

Although deployment of electrodes via leads 16 will be described for purposes of illustration, arrays of electrodes could be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, leads 16 carry electrodes that are placed adjacent to the target tissue of the spinal cord. Leads 16 may be implanted and coupled to an implanted stimulator 14. Alternatively, in some embodiments, leads 16 may be implanted and coupled to an external stimulator, e.g., through a percutaneous port. In additional embodiments, stimulator 14 may be a leadless stimulator with one or more arrays of electrodes arranged on a housing of the stimulator rather than leads that extend from the housing. Application of shifting techniques will be described with respect to implantable stimulator 14 and implantable leads 16 with ring electrodes for purposes of illustration.

In the example of FIG. 1A, stimulation energy is delivered to the spinal cord 18 to reduce the amount of pain perceived by patient 12. As mentioned above, however, the stimulator may be used with a variety of different pain therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation delivered by stimulator 14 may take the form of stimulation pulses or continuous stimulation waveforms, and may be characterized by controlled voltage levels or controlled current levels, as well as pulse width and pulse rate in the case of stimulation pulses.

Moreover, the stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 perceives the interruption of pain signals as a reduction in pain and, therefore, efficacious therapy.

With reference to FIG. 1A, a user, such as a clinician or patient 12, may interact with a user interface of external programmer 20 to program stimulator 14. Programming of stimulator 14 may refer generally to the generation and transfer of commands, programs, or other information to control the operation of the stimulator. For example, programmer 20 may transmit programs, parameter adjustments, program selections, group selections, or other information to control the operation of stimulator 14, e.g., by wireless telemetry. As one example, programmer 20 may transmit parameter adjustments to support parameter-directed shifting of electrode combinations used to deliver stimulation according to a selected program.

In some cases, external programmer 20 may be characterized as a physician or clinician programmer if it is primarily intended for use by a physician or clinician. In other cases, external programmer 20 may be characterized as a patient programmer if it is primarily intended for use by a patient. In general, a physician or clinician programmer may support selection and generation of programs by a clinician for use by stimulator 14, whereas a patient programmer may support adjustment and selection of such programs by a patient during ordinary use.

Stimulator 14 may be implanted in patient 12 at a location minimally noticeable to the patient. Alternatively, stimulator may be external with percutaneously implanted leads. For SCS, stimulator 14 may be located in the lower abdomen, lower back, or other location to secure the stimulator. Leads 16 are tunneled from stimulator 14 through tissue to reach the target tissue adjacent to spinal cord 18 for stimulation delivery. At the distal tips of leads 16 are one or more electrodes (not shown) that transfer the stimulation pulses from the lead to the tissue. The electrodes may be electrode pads on a paddle lead, circular (i.e., ring) electrodes surrounding the body of leads 16, conformable electrodes, cuff electrodes, segmented electrodes, or any other type of electrodes capable of forming unipolar, bipolar or multipolar electrode configurations. In general, ring electrodes arranged at different axial positions at the distal ends of leads 16 will be described for purposes of illustration.

External programmer 20 permits a user to shift the electrode combination used by a currently selected program along the length of leads 16 by adjusting a shift parameter. Each of the electrode combinations specifies a combination of electrodes arranged along lengths of two or more leads, and the parameter adjustment indicates a shift to the second electrode combination in a first direction along the lengths of the leads. If each lead 16 includes four electrodes, then the leads can be viewed as having four axial positions or levels.

In the orientation of FIG. 1A, the distal ends of leads 16 may be viewed as being upper while the more proximal regions of the leads may be viewed as being lower. If the electrodes are numbered 0 through 3 from the most distal to most proximal electrode, the left-handed lead is lead 0 and the right-handed lead is lead 1, and a given electrode combination includes electrode 2 on lead 0 and electrode 1 on lead 1, then an upward shift (in a proximal to distal direction) would result in an electrode combination of electrode 1 on lead 0 and electrode 0 on lead 1.

External programmer 20 presents an interface that permits this type of shift, and other shifts, by adjustment of a parameter value that corresponds to the electrode positions. In general, a parameter value may have four different values (1, 2, 3, and 4) which correspond to the four different possible levels of leads 16. Because an electrode cannot extend above the most distal position or below the most proximal position, however, the number of possible parameter values may be limited.

If an electrode combination includes electrode 2 on lead 0 and electrode 3 on lead 1, for example, it is not possible to shift any further toward the proximal end. In this case, external programmer 20 may limit the ability of the user to increase the shift parameter value to 4 because it would not be possible to provide a corresponding electrode combination.

Although electrodes may be numbered 0 to n, it may be desirable to represent the shift parameter value as a value from 1 to n, as a lay user may be confused by a parameter range that starts with a value of 0. Accordingly, in some embodiments, different shift positions may be indicated by values 1 to 4, rather than 0 to 3, or other values as determined by the actual number of shift positions available for a particular electrode combination, e.g., 1 to 2 or 1 to 3.

Figure 1B:
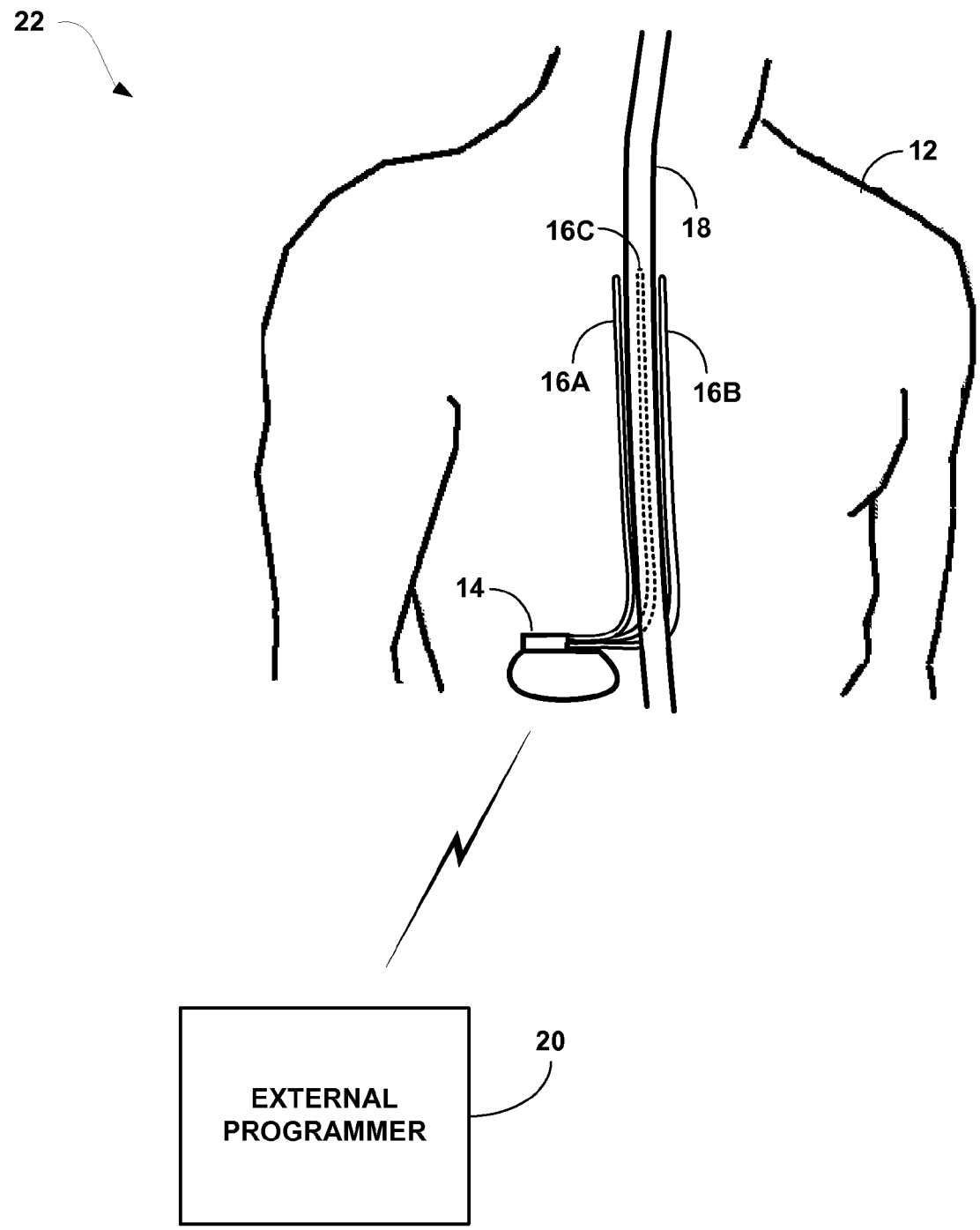
FIG. 1B is a schematic diagram illustrating an implantable stimulation system including a trio of implantable stimulation leads.

FIG. 1B is a schematic diagram illustrating an implantable stimulation system 22 including a trio of implantable stimulation leads 16A, 16B, 16C (collectively leads 16). System 22 generally conforms to system 10 of FIG. 1A, but includes a third lead. Accordingly, stimulator 14 may deliver stimulation via combinations of electrodes carried by all three leads 16, or a subset of the three leads. The third lead, e.g., lead 16C, may include a greater number of electrodes than leads 16A and 16B.

For example, leads 16A and 16B could include four electrodes, while lead 16C includes eight or sixteen electrodes. For purposes of parameter-directed shifting, two or more leads with different electrode counts may create a special problem. In particular, for every electrode that is shift on leads 16A, 16B, there may be two or more electrodes that required shifting on lead 16C in order to maintain the general integrity and shape of the electrical stimulation pattern delivered by the electrode combination.

As will be described, an external programmer 20 may be configured to execute shifts in steps, where the number of shift steps along the length of a lead having a greater electrode count is greater than the number of shift steps along the length of a lead having a lesser electrode count. If the leads 16 are numbered 0, 1 and 2, and the electrodes on leads 16A, 16B are numbered 0-4, while the electrodes on lead 16C are numbered 0-8, a shift step may involve shifting one step on leads 16A, 16B for every two steps on lead 16C.

For example, if the current electrode combination includes electrode 1 on lead 16A, electrodes 1 and 2 on lead 16C, and electrode 2 on lead 16B, then a first step in a distal to proximal direction may result in an electrode combination including electrode 2 on lead 16A, electrodes 2 and 3 on lead 16C, and electrode 3 on lead 16B.

Then, a second step in a distal to proximal direction may result in an electrode combination including electrode 2 on lead 16A, electrodes 3 and 4 on lead 16C and electrode 3 on lead 16B. In this manner, electrodes on lead 16C (with higher electrode count) are shifted in both steps, while electrodes on leads 16A and 16B (with lower electrode count) are only shifted during the first step. Alternatively, electrodes on leads 16A and 16B could be shifted in the second step and not the first step.

In any event, the number of shift steps is greater for lead 16C having the higher electrode count. In other words, programmer 20 shifts electrode position for the higher electrode count lead 16C in response to each shift parameter adjustment, but shifts electrode position for the lower electrode count leads 16A, 16B for every other shift parameter adjustment, i.e., on an alternating basis. A set of rules for determining the shift for leads with different electrode codes may vary according to the direction in which the shift is initiated, as will be described.

Figure 2:
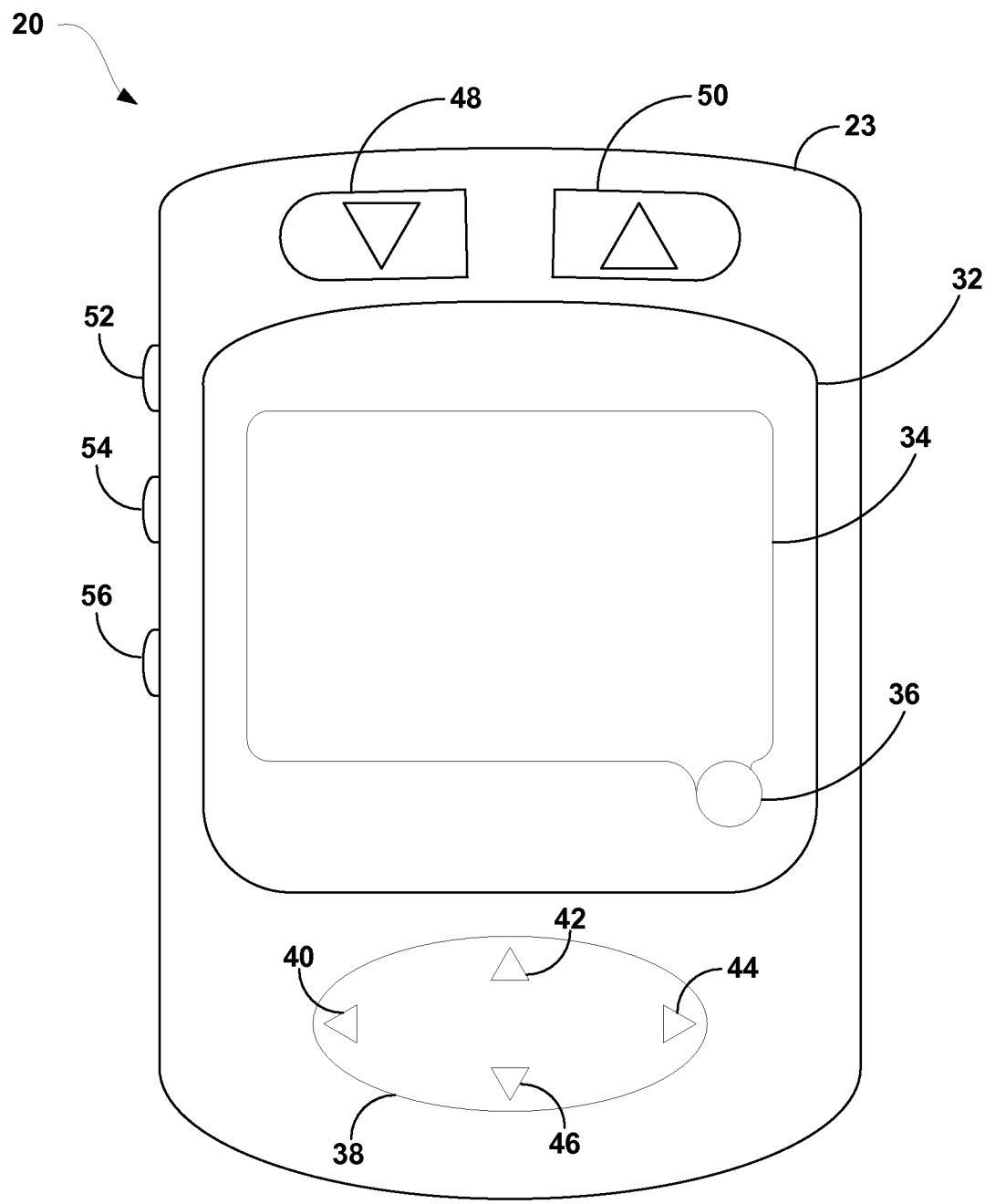
FIG. 2 is a conceptual diagram illustrating an example external programmer for programming stimulation therapy delivered by an implantable electrical stimulator.

FIG. 2 is a conceptual diagram illustrating an example external programmer 20 for programming stimulation therapy in an implantable electrical stimulator. In other embodiments, external programmer 20 may be used with an external electrical stimulator. As shown in FIG. 2, external programmer 20 provides a user interface for a user, such as patient 12, to manage and program stimulation therapy. Programmer 20 is protected by housing 23, which encloses circuitry necessary for the programmer to operate.

Programmer 20 also includes display 34, power button 56, increase button 50, decrease button 48, backlight button 36, and select buttons 52 and 54. Cover 32 protects screen 34 from being damaged during programmer 20 use. Programmer 20 also includes control pad 38 which allows a user to navigate through items displayed on display 34 in the direction of arrows 40, 42, 44 and 46. In some embodiments, the buttons and pad 38 may take the form of soft keys, with functionality that may change, for example, based on current programming operation or user preference.

In the illustrated embodiment, programmer 20 is a hand held device. Programmer 20 may be a patient programmer that may accompany patient 12 throughout a daily routine. In some cases, programmer 20 may be used by a clinician when patient 12 visits the clinician. In other embodiments, programmer 20 may be a clinician programmer that remains with the clinician or in the clinic, and is used by the clinician and/or patient 12 when the patient is in the clinic. In the case of a clinician programmer, small size and portability may be less important. Accordingly, a clinician programmer may be sized larger than a patient programmer, and may provide a larger screen for more full-featured programming.

Housing 23 may be constructed of a polymer, metal alloy, composite, or combination material suitable to protect and contain components of programmer 20. In addition, housing 23 may be partially or completely sealed such that fluids, gases, or other elements may not penetrate the housing and affect components therein. Power button 56 may turn programmer 20ON or OFF as desired by patient 12. Backlight button 36 may also control the illumination level, or backlight level, of display 34. In some embodiments, backlight 36 may be a knob that rotates clockwise and counter-clockwise to control programmer 20 operational status and display 34 illumination. Programmer 20 may be prevented from turning OFF during telemetry with stimulator 14 or another device to prevent the loss of transmitted data or the stalling of normal operation. Alternatively, programmer 20 and stimulator 14 may include instructions that handle possible unplanned telemetry interruption, such as battery failure or inadvertent device shutdown.

Display 34 may be a liquid crystal display (LCD) or similar monochrome or color display capable of providing information, such as a user interface, to patient 12. Display 34 may provide a user interface regarding current stimulation therapy, provide a therapeutic tree for programming stimulation therapy, provide a user interface for receiving feedback or medication input from patient 12, display an active group of stimulation programs, and display operational status of programmer 20. For example, programmer 20 may provide a scrollable list of groups, and a scrollable list of programs within each group, via display 34.

Control pad 38 allows patient 12 to navigate through items displayed on display 34. Patient 12 may press control pad 38 on any of arrows 40, 42, 44, and 46 in order to move to another item on display 34 or move to another screen not currently shown on the display. In some embodiments, pressing the middle of control pad 38 may select any item highlighted in display 34. In other embodiments, scroll bars, a touch pad, scroll wheel, individual buttons, or a joystick may perform the complete or partial functions of control pad 38.

Decrease button 48 and increase button 50 provide an input mechanism for patient 12. In general, decrease button 48 may decrease the value of a highlighted stimulation parameter every time the decrease button is pressed. In contrast, increase button 50 may increase the value of a highlighted stimulation parameter one step every time the increase button is pressed. While buttons 48 and 50 may be used to control the value of any stimulation parameter, buttons 48 and 50 may also control patient feedback input. For example, pressing increase button 50 may provide efficacy input indicating that the current stimulation program is reducing pain. Conversely, pressing decrease button 48 may provide efficacy input indicating that the current stimulation program is not reducing pain. In other embodiments, decrease button 48 and increase button 50 may only decrease and increase stimulation parameters while control pad 38 is used to receive efficacy feedback from patient 12 or a clinician.

Select buttons 52 and 54 may be configured to perform operational functions related to stimulation therapy or the use of programmer 20. For example, buttons 52 and 54 may control the volume of audible sounds produced by programmer 20, wherein button 52 increases the volume and button 54 decreases the volume. Button 56 may be pressed to enter an operational menu that allows patient 12 to configure the user interface of programmer 20 to the desires of patient 12. For example, patient 12 may be able to select a language, backlight delay time, display 34 brightness and contrast, or other similar options. In alternative embodiments, buttons 48 and 50 may control all operational and selection functions, such as those related to audio volume or stimulation therapy. Alternatively, buttons 52 and 54 may be programmed to allow the user to turn stimulation ON and OFF.

Programmer 20 may take other shapes or sizes not described herein. For example, programmer 20 may take the form of a clam-shell shape, similar to cellular phone designs. When programmer 20 is closed, some or all elements of the user interface may be protected within the programmer. When programmer 20 is opened, one side of the programmer may contain a display while the other side may contain input mechanisms. In any shape, programmer 20 may be capable of performing the requirements described herein. Alternative embodiments of programmer 20 may include other input mechanisms such as a keypad, microphone, camera lens, or any other media input that allows the user to interact with the user interface provided by programmer 20.

In alternative embodiments, the buttons of programmer 20 may perform different functions than the functions provided in FIG. 2 as an example. In addition, other embodiments of programmer 20 may include different button layouts or number of buttons. For example, programmer 20 may even include a single touch screen that incorporates all user interface functionality.

Figure 3:
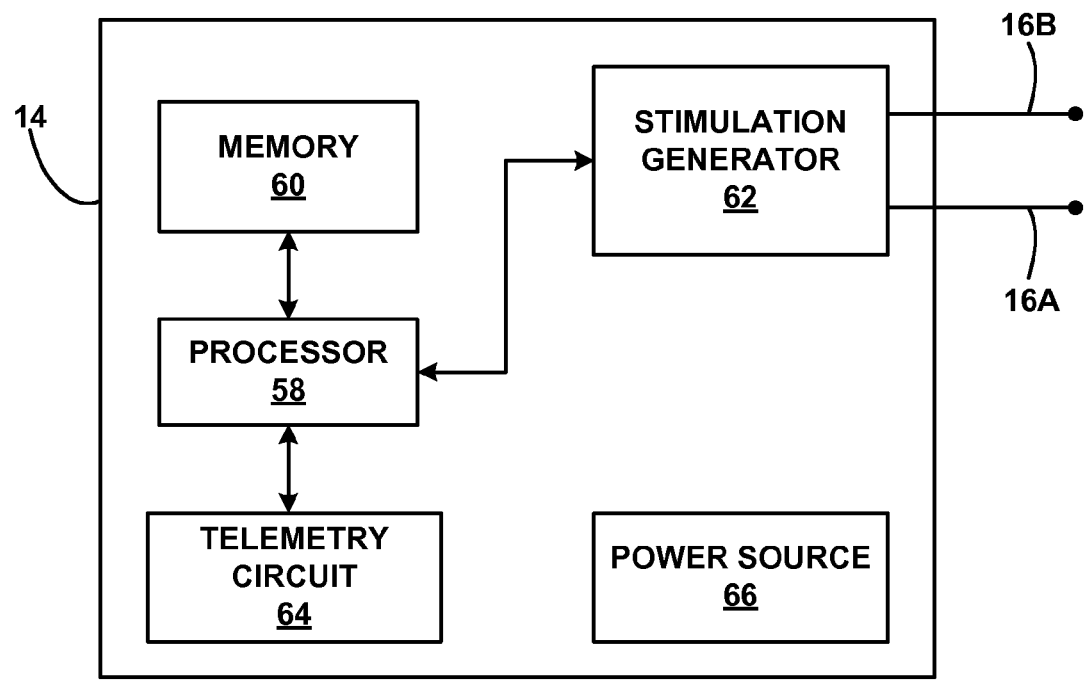
FIG. 3 is a functional block diagram illustrating various components of an implantable electrical stimulator.

FIG. 3 is a functional block diagram illustrating various components of an implantable stimulator 14. In the example of FIG. 3, stimulator 14 includes a processor 58, memory 60, stimulation signal generator 62, telemetry circuit 64, and power source 66. Memory 60 may store instructions for execution by processor 58, stimulation therapy data, efficacy feedback, and any other information regarding therapy or patient 12. Therapy information may be recorded for long-term storage and retrieval by a user, and adjustment of the program path of the therapeutic tree. Memory 60 may include separate memories for storing instructions, the therapeutic tree, program path, and program histories.

Processor 58 controls stimulation generator 62 to deliver electrical stimulation via electrode combinations formed by electrodes in one or more electrode arrays. For example, stimulation generator 62 may deliver electrical stimulation therapy via electrodes on one or more leads 16, e.g., as stimulation pulses or continuous waveforms. Stimulation generator 62 may include stimulation generation circuitry to generate stimulation pulses or waveforms and switching circuitry to switch the stimulation across different electrode combinations, e.g., in response to control by processor 58. In particular, processor 58 may control the switching circuitry on a selective basis to cause stimulation generator 62 to deliver electrical stimulation to selected electrode combinations and to shift the electrical stimulation to different electrode combinations in a first direction or a second direction, as described herein, in a series of shift operations.

As an example, an electrode combination may be represented by a data stored in a memory location, e.g., in memory 60, of stimulator 14. Processor 58 may access the memory location to determine the electrode combination and control stimulation generator 62 to deliver electrical stimulation via the indicated electrode combination. To shift from the present electrode combination, e.g., in response to a shift command sent by programmer 20 in response to a shift parameter adjustment by a user, processor 58 may rewrite the memory location to indicate a different electrode combination to which electrical stimulation should be shifted. In general, the first and second electrode combinations may substantially conform to one another in terms of pattern. Pattern may refer to the relative positions and spacing between active electrodes (i.e., the cathodes and anodes) in an electrode combination.

The second electrode combination may present a substantially similar pattern as the first electrode combination in terms of relative positions of active electrodes and relative spacing between the active electrodes. The pattern presented by a first electrode combination and a second electrode combination to which electrical stimulation is shifted may be substantially identical. In some cases, however, the pattern may be substantially similar but slightly different. For example, for lead configurations with different electrode counts, or other electrode arrays with different electrode counts, electrode spacings between first and second electrode combinations may be slightly different.

To accommodate lead configurations with different electrode counts, spacing between some of the electrodes in the first and second electrode combinations may vary. With a 4-8-4 lead configuration, for example, shifting may include more shift steps on the 8-electrode lead than on the 4-electrode leads. In particular, there may be two shift steps on the 8-electrode lead for every single step on the 4-electrode lead, so that the electrical stimulation pattern can be generally preserved. In this case, the electrical stimulation pattern may be identical for some shifts and slightly different for other shifts, e.g., on an alternating basis. Processing of parameter-directed shifting for lead configurations with different electrode counts is described below with respect to FIGS. 9-14.

The shift command transmitted by programmer 20 may identify the shift parameter value, the particular electrode combination to which stimulation should be shifted, a command indicating an incremental shift and a direction of the shift, or some other form of shift command sufficient to cause stimulator 14 to shift from one electrode combination to another electrode combination. In operation, in response to a shift command, processor 58 may rewrite the memory location to indicate the new electrode combination. In particular, in some embodiments, processor 58 may cause stimulation generator 62 to turn OFF stimulation on the present electrode combination, rewrite the memory location to indicate the new electrode combination, and then turn stimulation back ON, in which case stimulation generator 62 delivers stimulation to the new electrode combination indicated in the memory location. Hence, when stimulation is turned ON, processor 58 or stimulation generator may access the memory location to identify the present electrode combination and then deliver stimulation via that combination.

In other embodiments, rather than rewriting a single memory location, processor 58 may make use of two or more memory locations, where one memory location indicates a first electrode combination and the other memory location indicates a second electrode combination. In this case, processor 58 may alternately access the first and second memory locations to shift electrode combinations in response to a shift command. For example, processor 58 may access the first memory location to deliver stimulation via a first electrode.

In response to a shift command, processor 58 may rewrite the second memory location to indicate the new electrode combination and then access the second memory location to shift to that new electrode combination, e.g., after turning OFF stimulation on the first electrode combination and before turning stimulation ON again. Alternatively, in some embodiments, stimulation on a first electrode combination may be ramped down while stimulation on the second electrode combination is ramped up, i.e., in at least a partially overlapping manner or on an alternating, interleaved basis over a series of time slots. Then, in response to another shift command, processor 58 may rewrite the first memory location to indicate another new electrode combination, and then access the first memory location to shift to that new electrode combination. In effect, processor 58 may toggle back and forth between the first and second memory locations, alternating writing and reading the locations to shift electrical stimulation among different electrode combinations.

In other embodiments, processor 58 may make use of two or more memory locations within memory 60, where at least a first memory location stores a first electrode combination and a second memory location stores a second electrode combination. These electrode combinations may be pre-loaded, or pre-configured, within the memory locations in memory 60. In this case, processor 58 may switch between different memory locations, such as the first and second memory locations, when selecting electrode combinations in response to receiving one or more shift commands from programmer 20. In response to receiving such a shift command, for example, processor 58 may switch from reading the first memory location to reading the second memory location within memory 60 to select the second electrode combination stored in the second memory location. Procedurally, processor 58 may turn OFF stimulation for the electrode combination stored in the first memory location, switch to the second memory location to select the second electrode combination, and then turn ON stimulation for the second electrode combination, or may interleave delivery of stimulation via the first and second electrode combinations as described above.

Hence, processor 58 may rewrite and access a single memory location that serves as a master location for the active electrode combination, or the electrode combination to be activated upon shifting. Alternatively, processor 58 may use two or more memory locations. In each case, the data stored at the memory location(s) specifies the electrode combination, e.g., in terms of identifying particular active electrodes on one or more leads, as well as associated electrode polarities. When activating stimulation, processor 58 may access not only the memory location specifying the electrode combination but also other memory locations specifying various stimulation parameters such as voltage or current amplitude, pulse width and pulse rate. Stimulation generator 62, e.g., under control of processor 58, then makes use of the electrode combination and parameters in formulating and delivering the electrical stimulation to the patient. Processor 58 also may control telemetry circuit 64 to send and receive information. For example, telemetry circuit 64 may send information to and receive information from an external device, such as programmer 20. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

Processor 58 stores stimulation parameters in memory 60, e.g., as programs and groups of programs. Upon selection of a particular program group, processor 58 may control stimulation generator 62 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

In accordance with this disclosure, stimulator 14 may be responsive to adjustment of a shift parameter by a user via programmer 20. In particular, processor 58 may receive a shift parameter adjustment from programmer 20 via telemetry circuit 64, and shift the electrode combination for a selected program in response to the shift parameter adjustment. Stimulator 14 may execute parameter-directed shifting of electrode combinations in response to parameter adjustments received from programmer 20. In this manner, stimulator 14 may permit the patient 12 to make parameter-directed electrode combination shifts to maintain or improve therapeutic efficacy.

Wireless telemetry in stimulator 14 with external programmer 20 or another device may be accomplished by radio frequency (RF) communication or proximal inductive interaction of stimulator 14 with external programmer 20. Telemetry circuit 64 may send information to and receive information from external programmer 20 on a continuous basis, at periodic intervals, or upon request from the stimulator or programmer. To support RF communication, telemetry circuit 64 may include appropriate electronic components, such as amplifiers, filters, mixers, encoders, decoders, and the like.

Power source 66 delivers operating power to the components of stimulator 14. Power source 66 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional batteries may be used for a limited period of time. As a further alternative, an external inductive power supply could transcutaneously power stimulator 14 when needed or desired.

Figure 4:
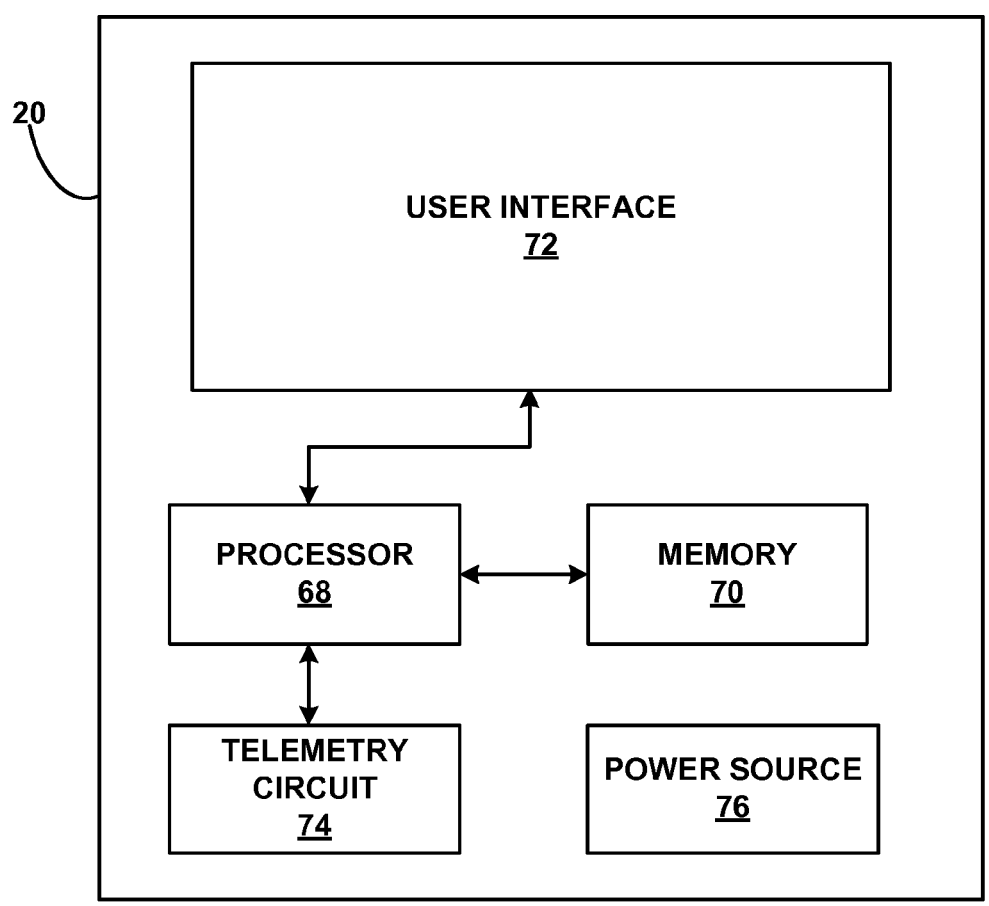
FIG. 4 is a functional block diagram illustrating various components of an external programmer for an implantable stimulator.

FIG. 4 is a functional block diagram illustrating various components of an external programmer 20 for an implantable stimulator 14. As shown in FIG. 4, external programmer 20 includes processor 68, memory 70, telemetry circuit 74, user interface 72, and power source 76. A clinician or patient 12 interacts with user interface 72 in order to manually change the program path, adjust voltage or current amplitude, change weighting (i.e., prioritization or level) of stimulation parameter types within the therapeutic tree, provide efficacy feedback, or view stimulation data.

User interface may include a screen and one or more input buttons, as shown in FIG. 2, that allow external programmer 20 to receive input from a user. As shown in FIG. 2, the screen may be a liquid crystal display (LCD), dot matrix display, or touch screen. The input buttons may include a touch pad, increase and decrease buttons, emergency shut off button, and other buttons needed to control the stimulation therapy, as described above with regard to FIG. 2. Processor 68 controls user interface 72, retrieves data from memory 70 and stores data within the memory. Processor 68 also controls the transmission of data through telemetry circuit 74 to stimulator 14. Memory 70 includes operation instructions for processor 68 and data related to the structure of the therapeutic tree and currently chosen program path.

Telemetry circuit 74 allows the transfer of data to and from stimulator 14. Telemetry circuit 74 may communicate automatically with stimulator 14 at a scheduled time or when the telemetry circuit detects the proximity of the stimulator. Alternatively, telemetry circuit 74 may communicate with stimulator 14 when signaled by a user through user interface 72. To support RF communication, telemetry circuit 74 may include appropriate electronic components, such as amplifiers, filters, mixers, encoders, decoders, and the like. Power source 76 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 5:
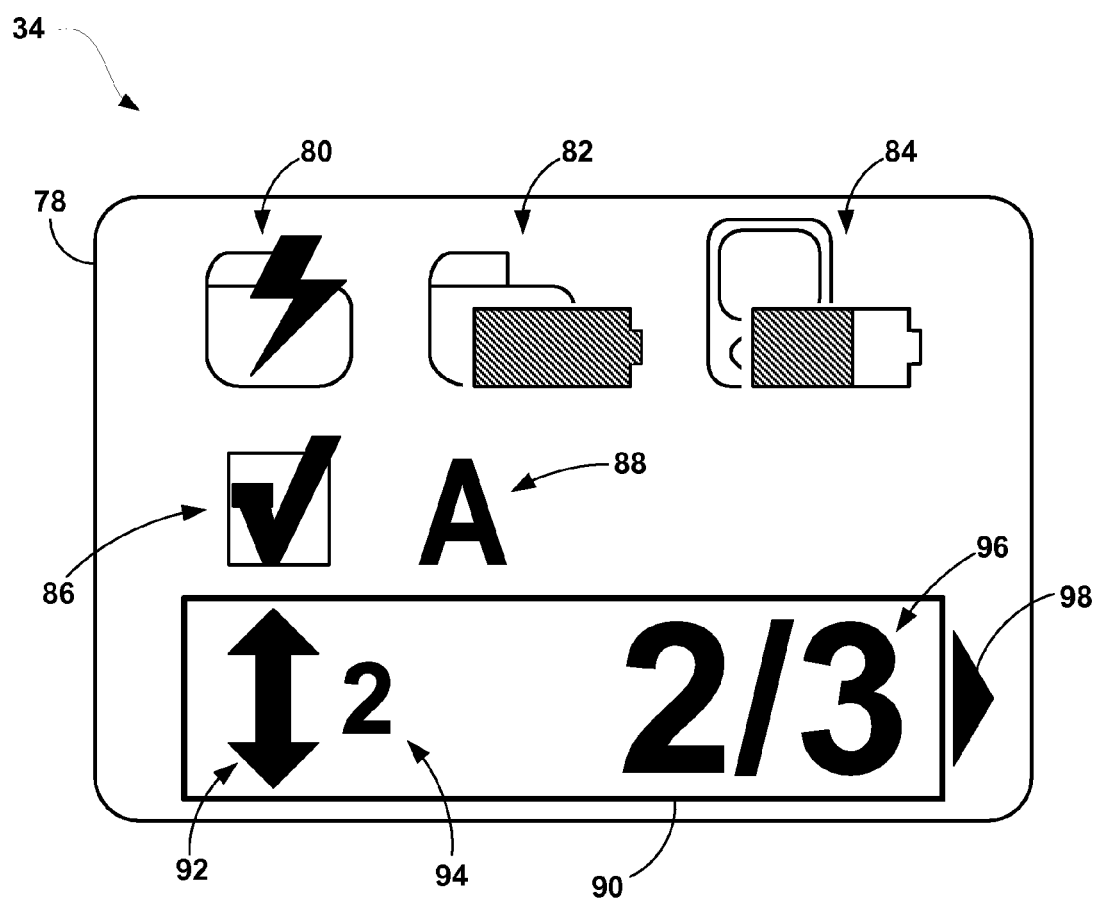
FIG. 5 is a conceptual diagram illustrating an example user interface of an external programmer for receiving input indicating various electrical stimulation parameter adjustments.

FIG. 5 is a conceptual diagram illustrating an example user interface of an external programmer for receiving input indicating various electrical stimulation parameter adjustments. In the example of FIG. 5, display 34 of programmer 20 provides user interface 78 to the user, such as patient 12. User interface 78 includes group identifier 88, group selection icon 86, information box 90, up/down arrow 92, program identifier 94, stimulation icon 80, battery icon 82, programmer battery icon 84, electrode combination shift parameter value 96, and navigation arrow 98. User interface 78 provides information to patient 12 regarding group, program and electrode combination status. More or less information may be provided to patient 12, as desired by the clinician or patient.

Group identifier 88 indicates one of possibly several groups of programs that can be selected for delivery to patient 12. Group selection icon 86 indicates whether the displayed group, e.g., group A in FIG. 5, is actually selected for delivery to patient 12. If a presently displayed group is selected, group selection icon 86 includes a box with a checkmark. If a presently displayed group is not selected, group selection icon 86 includes a box without a checkmark. To navigate through the program groups, a user may use control pad 38 to select the group identifier 88 and then use control pad 38 to scroll through the various groups, e.g., A, B, C, and so forth. Stimulator 14 may be programmed to support a small number of groups or a large number of groups, where each group contains a small number of programs or a large number of programs that are delivered simultaneously, in sequence, or on a time-interleaved basis.

For each group, group selection icon 86 indicates the appropriate status. For a given group, program identifier 94 indicates one of the programs associated with the group. A user may select up-down arrow 92 and actuate control pad 38 to scroll through the different programs in a group, e.g., 1, 2, 3, and so forth. For example, the user may use arrows 40 and 44 to navigate though programs available for stimulation. A given group may include a small number of programs or a large number of programs. For a given program, information box 90 presents a shift parameter value 96 indicating a particular electrode combination shift position.

In the example of FIG. 5, a particular set of leads provides three different shift positions for an electrode combination associated with program 2. In this example, shift parameter value 96 indicates that the electrode combination is presently at shift position two out of three possible positions (2/3). The shift parameter value may be presented in this X/Y format, where X indicates the number of shifts from the most proximal electrode that corresponds to the position of the current electrode combination, and Y indicates the number of electrode shifts that are possible for the electrode combination, given the applicable electrode and lead configuration. A shift parameter value of 3 may indicate a most distal shift position while a shift parameter value of 1 indicates a most proximal shift position, relative to proximal and distal ends of the leads. Alternatively, the opposite may be implemented such that a shift parameter value of 3 may indicate a most proximal shift position while a shift parameter value of 1 indicates a most distal shift position, relative to proximal and distal ends of the leads. In each case, for three possible shift positions, a shift parameter value of 2 indicates a middle shift position.

In the event that the user directs the parameter value 96 to shift beyond the last shift position, the parameter value may continue to the shift position at the other end of the lead. For example, a directed shift above position (3/3) may change the position to (1/3). Conversely, a directed shift below position (1/3) may change the position to (3/3). Alternatively, user interface 78 may prevent any change in position beyond the presented upper or lower position limit.

The maximum shift parameter value, and hence the number of possible shift positions, may vary according to the shape of the electrical stimulation pattern delivered via the electrode combination in terms of the positions of the electrodes. If all electrodes for an electrode combination are at the same level, then a maximum number of shift positions is possible. For example, if each of two leads includes four electrodes, and an electrode combination includes electrode 0 on lead 0 (0/0) and electrode 0 on lead 1 (0/1), then there are four possible shift positions: (0/0, 0/1); (1/0, 1/1); (2/0, 2/1); and (3/0, 3/1). In this case, the electrode combinations (0/0, 0/1), (1/0, 1/1), (2/0, 2/1), and (3/0, 3/1) may be represented by the shift parameter values of 1/4, 2/4, 3/4, 4/4, respectively. Alternatively, depending on desired orientation, electrode combinations (0/0, 0/1), (1/0, 1/1), (2/0, 2/1), and (3/0, 3/1) may be represented by the shift parameter values of 4/4, 3/4, 2/4, 1/4, respectively. Orientation may be subject to design considerations. However, each shift parameter value corresponds to one of the possible shift positions in this example.

If some of the electrodes are on different levels, however, the maximum number of shift positions is reduced to avoid shifting one of the electrodes beyond the most distal or most proximal electrode position. For example, if each of two leads includes four electrodes, and an electrode combination includes electrode 1 on lead 0 (1/0) and electrode 2 on lead 1 (1/1), then there are only three possible shift positions: (0/0, 1/1); (1/0, 2/1); (2/0, 3/1). These electrode combinations may correspond, for example, to shift parameter values of 1/3, 2/3, 3/3. In particular, it is not possible to shift the electrode on lead 0 below the 0 position, just as it is not possible to shift the electrode on lead 1 beyond the 3 position. The number of possibilities may be further reduced if electrodes on the leads are two or more electrode levels apart. The same issue arises for electrodes on the same lead, e.g., 0/0 and 1/0 forming an electrode combination. Hence, the number of possible shift positions may vary as a function of the shape of the electrical stimulation delivered by the electrode combination, e.g., in terms of numbers of electrodes and distances between electrodes along the lengths of the leads.

In addition, the user may desire to limit the number of shifts available for a particular program. For example, a program may utilize an electrode combination that may have four different positions along the leads implanted within patient 12. However, the user may predominantly use only two of the four positions during therapy. In this manner, the user may tag the used shift positions as a playlist, for example, in which the unused shift positions never appear to the user during a shift operation. In this example playlist, only positions (0/3) and (1/3) are provided to the user. Positions (2/3) and (3/3) are not included in the playlist, and therefore not provided as options to the user.

In general, information box 90 presents information about the current program, e.g., program 2, for a given group and the current electrode combination shift position for that program, e.g., 2/3. Stimulation icon 80 indicates the current status of stimulation therapy. In FIG. 5, the bolt is shown to indicate that stimulation is being actively delivered to patient 12 according to the active program group, i.e., group A. In the case that stimulation is not being delivered, the bolt in icon 80 may not be shown. Stimulator battery icon 82 indicates the status of the battery in stimulator 14, which currently indicates that the battery is fully charged, or has a full charge in the case that the battery is not rechargeable. The status of the stimulator battery may be communicated from stimulator 14 to programmer 20 by wireless telemetry. In other embodiments, a percentage of battery life or battery life time remaining may be shown by stimulator battery icon 82. Similar to stimulator battery icon 82, programmer battery icon 84 indicates the status of the battery in programmer 20. Currently, programmer battery icon 84 displays that the programmer battery has approximately two-thirds charge remaining. In alternative embodiments, other status indications may be used to show a percentage or time remaining of the programmer battery.

When the user wishes to make a parameter-directed shift of electrode combination, the user selects the pertinent program 94 within the current group, and then selects the electrode combination shift parameter value 96. In the example of FIG. 5, the user selects increase button 50 or decrease button 48 (FIG. 2) to shift the electrode combination. Alternatively, the user may select arrow 98 to go to another screen associated with shifting the electrode combination. The first screen shown in FIG. 5 may be considered a navigation screen in the sense that it permits the user to select a particular program for application of parameter-directed shifting of electrode combinations.

The next screen, e.g., as shown in the examples of FIGS. 6A-6D, may be considered a programming screen in the sense that it permits the user to perform parameter-directed shifting of electrode combinations. However, the use of a separate screen is merely exemplary. In some embodiments, the user may rely on a single screen. For example, a preferred embodiment may involve a sequence of screens in FIGS. 5 and 6A-6D. In user interface 78, the user may press increase button 50 (FIG. 2) to shift the electrode combination up to the next position. Upon pressing increase button 50, the user may be presented with screen 35D of FIG. 6D to confirm the requested increase in shift position. If confirmed, the user may be presented with screen 35A of FIG. 6A to increase the amplitude of the stimulation. Other sequences of screens may be presented to the user according to the type of stimulation therapy or desires of the clinician or patient 12.

Figure 6A:
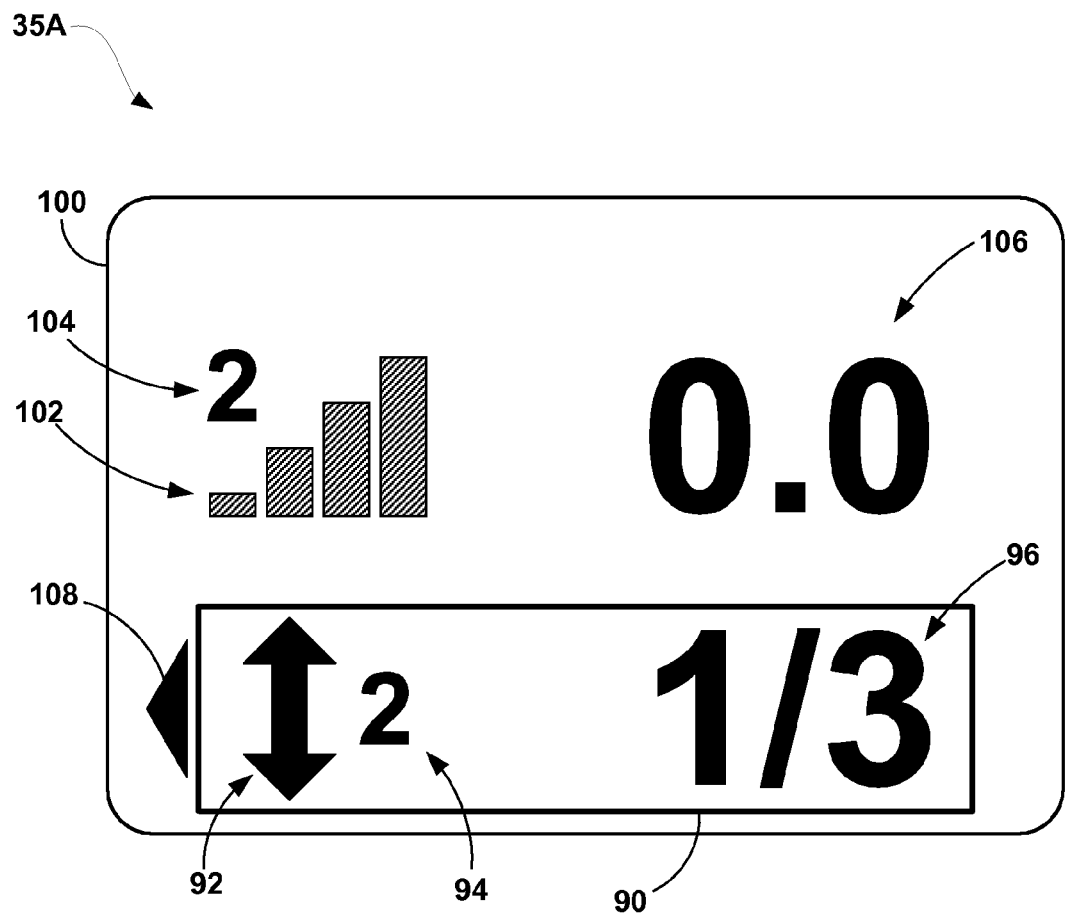
FIG. 6A is a conceptual diagram illustrating an example user interface of an external programmer for receiving parameter-directed input indicating desired shifting of electrode combinations by incrementing or decrementing an alphanumeric parameter value.
Figure 6B:
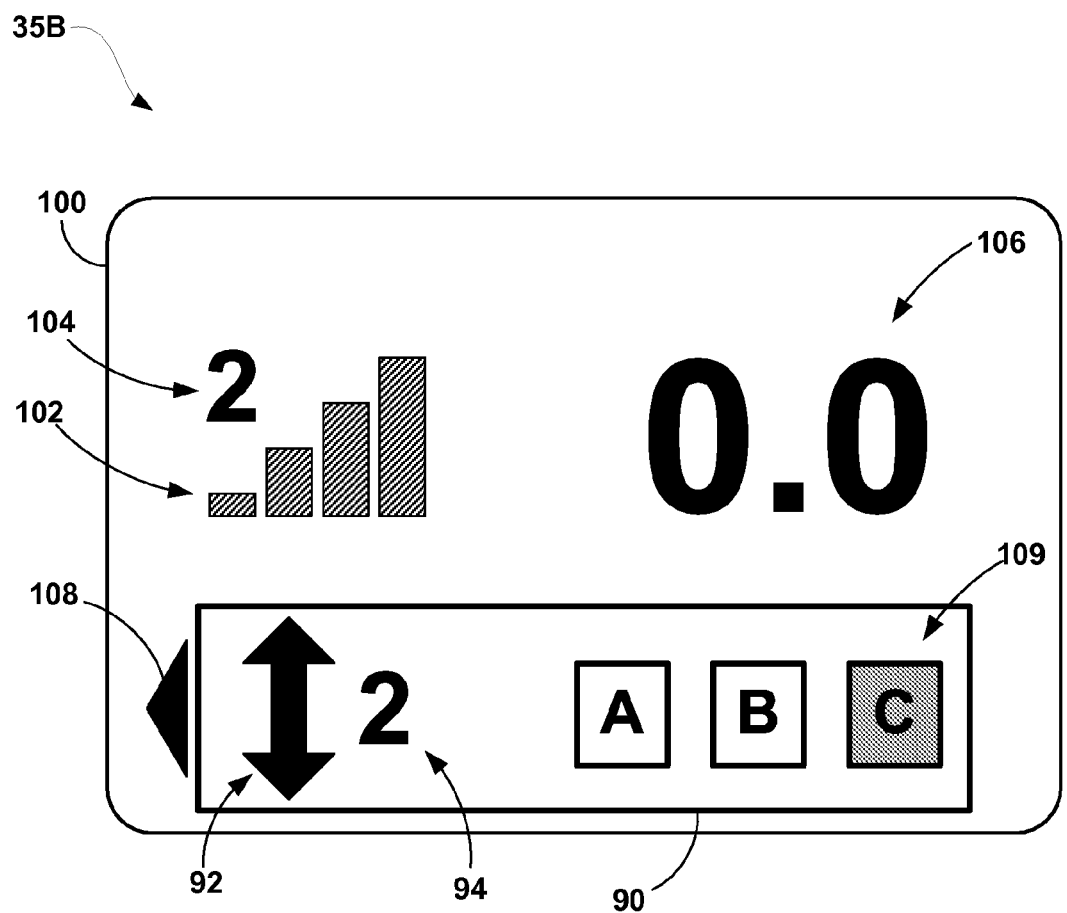
FIG. 6B is a conceptual diagram illustrating an example user interface of an external programmer for receiving parameter-directed input indicating desired shifting of electrode combinations by selecting an alphanumeric parameter value.
Figure 6C:
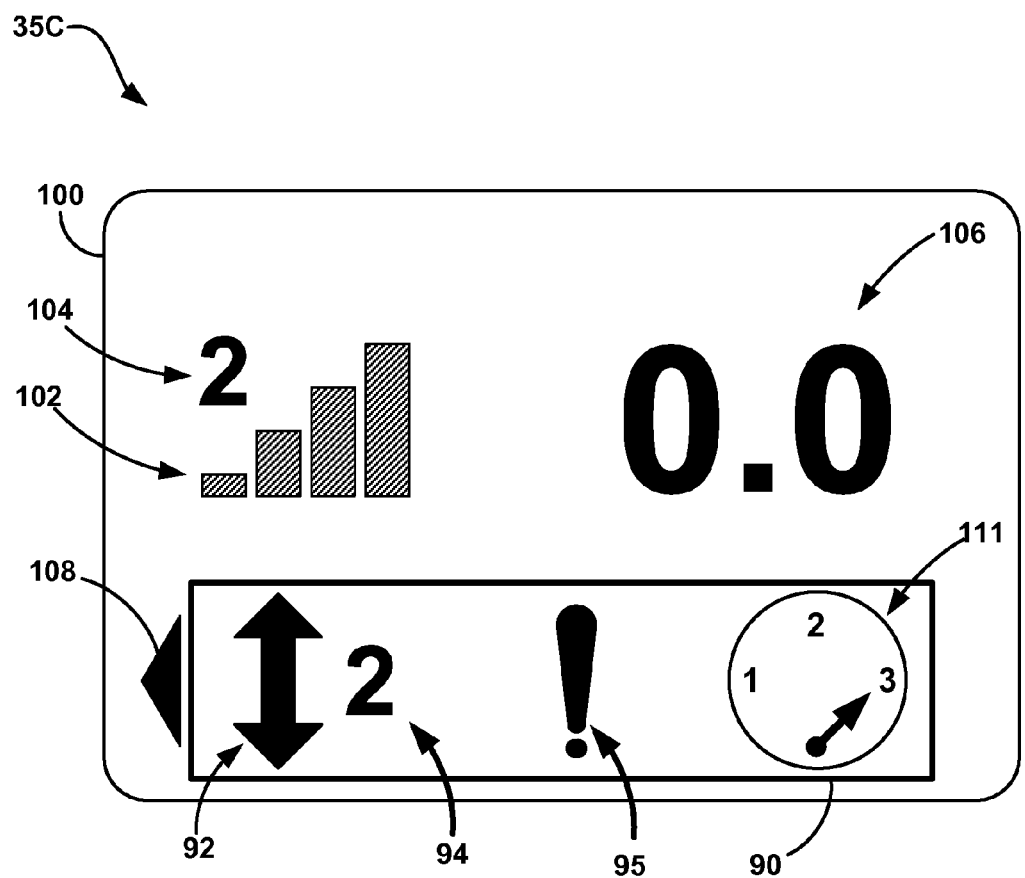
FIG. 6C is a conceptual diagram illustrating an example user interface of an external programmer for receiving parameter-directed input indicating desired shifting of electrode combinations by adjusting a radial pointer dial to an alphanumeric parameter value.

FIGS. 6A-6C are examples of a user interface of an external programmer 20 for receiving input indicating parameter-directing shifting of electrode combinations. A user may access the screens of FIGS. 6A-6C upon selecting the shifting parameter value 96 and then selecting arrow 98. In response, programmer 20 may present screen 35A for execution of parameter-directed shifting by the user. FIG. 6A illustrates parameter-directed shifting of electrode combinations by incrementing or decrementing an alphanumeric parameter value. FIG. 6B illustrates parameter-directed shifting of electrode combinations by selecting an alphanumeric parameter value. FIG. 6C illustrates parameter-directed shifting of electrode combinations by adjusting a radial pointer dial to an alphanumeric parameter value. FIGS. 6A-6C provide examples of various parameter-directed techniques for electrode shifting for purposes of illustration, but without limitation of the techniques broadly embodied and described in this disclosure. In each of the examples of FIGS. 6A-6C, a user adjusts a parameter value, e.g., by adjusting a value or selecting a different value, each of which may be referred to generally as parameter adjustment. Each parameter value generally corresponds to a desired shifting of an electrode combination.

In the example of FIG. 6A, screen 35A includes information box 90 with the up/down arrow 92 to select different programs within a group, a program value 94 indicating the currently selected program within the group, and the shifting parameter value 96 indicating the currently selected shift position of the electrode combination associated with the selected program in the group. Amplitude icon 102 indicates that amplitude programming is available in screen 35A. Numeral 104 indicates the currently selected program (2) for amplitude programming, and value 106 indicates the current amplitude value for the stimulation delivered according to the program.

Icon 102 indicates that amplitude programming is available on screen 35A. In particular, a user may select amplitude value 106 and increase or decrease the current value. Arrow 108 may be selected to return to the previous screen, e.g., screen 34 of FIG. 5. When the electrode combination is changed, the program may ramp stimulation down to 0.0 on the electrode combination at the current shift position, as indicated in FIG. 6A, and then ramp stimulation up to a desired value on the electrode combination at the newly selected shift position. As one example, the ramp down to zero may be performed as an auto-ramp in the following percentages of the original amplitude: 100%, 95%, 89%, 82%, 73%, 63%, 50%, 32%, 15% and 0%. User may select the shift parameter value 96, e.g., using select buttons 52 or 54, and then adjust the shift parameter value using the increase or decrease buttons 48, 50, respectively. Other input media such as a stylus, scroll wheel, track ball, touchpad, touchscreen or the like may be use in a similar manner to select and adjust the shift parameter value.

During auto-ramping, programmer 20 may highlight, place a cursor around, or otherwise select the present amplitude value 106. If the user selects an increase or decrease key or button during auto-ramping, programmer 20 may cause stimulator 14 to terminate the auto-ramping process. In this case, the amplitude of the shifted electrode combination may be the amplitude applicable when the user selected the increase or decrease button. If the auto-ramp reaches the amplitude of the previous electrode combination, then auto-ramping likewise ceases. If auto-ramping is not active or is not made available, in some embodiments, programmer 20 may permit the user to adjust the amplitude in manual increments by highlighting amplitude 106 and selecting the increase or decrease keys. Also, the user may select another shift by increasing or decreasing the shift parameter value. If arrow 108 is selected during auto-ramping, then auto-ramping may be terminated.

For each adjustment to the shift parameter value, e.g., from 0/3 to 1/3 to 2/3 to 3/3 and so forth, programmer 20 may send a command to stimulator 14 indicating the pertinent shift position. In response, stimulator 14 ramps down amplitude on the electrode combination for the previous shift positions and then ramps up amplitude on the electrode combination for the new shift position. Alternatively, stimulator 14 may immediately zero the amplitude on the first electrode combination and then ramp the amplitude or set the amplitude to a value on the second electrode combination. In some embodiments, stimulator 14 may control the ramping process on an automated basis. In other embodiments, programmer 20 may control the ramping process by sending a series of commands over time, rather than just sending a command indicating the desired shift.

The up-ramp and down-ramp may occur simultaneously in an overlapping manner, or on a time-interleaved basis such that successive pulses or bursts of pulses alternate between the electrode combination corresponding to the first shift position and the electrode combination corresponding the next shift position. For example, a succession of gradually decreasing pulses or bursts may be applied to the first electrode combination while a succession of gradually increasing pulses or bursts is applied to the next electrode combination, e.g., on an alternating basis or simultaneously. Alternatively, stimulation amplitude may be fully ramped down on one electrode combination before stimulation begins to ramp up on the next electrode combination. In other examples, stimulation amplitude may be fully ramped up on a second electrode combination before stimulation begins to ramp down on the first, previous electrode combination.

Notably, in some embodiments, the user need not shift directly from one adjacent electrode combination to another, e.g., from 1 to 2, or from 2 to 3. Rather, in some embodiments, the user may increase the shift parameter value directly from one value to another value, e.g., 0 to 3 or 3 to 1, even though one or more intermediate values may lie between the values. In this manner, in some embodiments, the user may make smaller shift steps or larger shift steps, as desired. Additional user interface media may be provided to permit the user to step between different shift positions before actually activating stimulator 14 to deliver stimulation. For example, a user may adjust the shift parameter value from 1 to 3, and then activate stimulation, so that stimulation is not automatically delivered to electrode combinations at intermediate shift positions, such as 2.

In the example of FIG. 6A, the shift parameter value is a numeric value that indicates the current shift position out of a possible number of shift positions. The maximum shift position (3 in FIG. 6A) may correspond to the most distal shift position that can be achieved given the shape of the particular electrode combination assigned to the current program. Likewise, the minimum shift position value may correspond to the most proximal shift position that can be achieved for the given electrode combination. As an alternative, the values can be reversed such that the maximum value corresponds to most proximal and the minimum value corresponds to most distal. As a further alternative, in some embodiments, the alphanumeric shift parameter value may be presented as simply the shift position number without indicating the maximum shift position parameter value. For example, a 1 could be display instead of a 1/3.

In any event, the shift parameter value presents a parameter-directed indication of shift position. The shift parameter value may be an alphanumeric character or some other graphical or textual symbol, icon, or character that can be adjusted or selected to designate a different shift position. In each case, the parameter value corresponds to an electrode combination or shift position, but may not explicitly or directly indicate a position of the second electrode combination or a direction of the shift.

Instead, a particular electrode combination may be identifiable with a particular shift parameter value, but not on the basis of direction or position. In the example of FIG. 6A, for example, the shift parameter values of 1/3 or 2/3 do not explicitly indicate a spatial position or direction. Instead, these shift parameter values refer to different electrode combinations, much like different letters or numbers may be specified to select different groups, programs, amplitudes, pulse widths, pulse rates, or the like.

Using a shift parameter value, external programmer 20 may permit a patient or other user to shift electrode combinations in a manner similar to adjustments of other parameters, such as amplitude, pulse width or pulse rate. Parameter-directed shifting of electrode combinations may provide a simple and convenient interface that enables the patient to maintain or improve therapeutic efficacy, particularly when perceived therapeutic efficacy is reduced due to posture, position, activity, lead migration, accommodation or other factors.

FIG. 6B illustrates a screen 35B that conforms substantially to screen 35A of FIG. 6A. In the example of FIG. 6B, however, screen 35B provides a parameter value selection field 109 instead of adjustable shift parameter value 96. Using screen 35B, patient 12 or another user selects one of the boxes in selection field 109 to adjust the current shift parameter value, e.g., from A to B, A to C, B to C, and so forth. In this manner, the user selects the shift parameter value from a plurality of shift parameter values. FIG. 6B illustrates another example of an alphanumeric shift parameter value set, A, B, C. In the example of FIG. 6A, shift parameter values are illustrated as numbers. In other embodiments, shift parameter values may be expressed as numbers, letters, combinations of numbers and letters, symbols, icons, and the like. In addition, although FIGS. 6A-6C illustrate visual media, shift parameter values may be presented and adjusted via audible, tactile or other media, or via combinations of visual, audible and/or tactile media.

FIG. 6B also illustrates the selection of shift parameter values from a group of parameter values presented simultaneously to the user in selection field 109, in contrast to adjustment of a shift parameter value, e.g., by increasing or decreasing the value. In each case, however, the adjustment of selection of a shift parameter value may be referred to as a shift parameter adjustment. Upon selection of one of the shift parameter values to adjust the shift parameter value, e.g., from shift position A to shift position C, programmer 20 may generate a command and transmit the command to stimulator 14 to cause the stimulator to execute the indicated shift of the electrode combination associated with the selected program within the current program group.

In general, programmer 20 may cause stimulator 14 to perform various operations by generating and sending multiple commands to the stimulator via wireless telemetry, or sending a single command that triggers the performance of multiple operations by the stimulator. For example, in some embodiments, programmer 20 may send a series of commands that control electrode shifting by stimulator 14 as well as each of a series of steps in ramping stimulation amplitude down for one electrode combination and up for another electrode combination. Alternatively, in other embodiments, programmer 20 may send a single command that indicates a particular shift and triggers stimulator 14 to carry out the shift and each of the operations necessary to affect the shift, such as various ramping operations, without the need for individual commands for each operation.

FIG. 6C illustrates another screen 35C that conforms substantially to screens 35A and 35B of FIGS. 6A and 6B. In the example of FIG. 6C, however, screen 35C provides yet another example technique for parameter value adjustment. In particular, FIG. 6C illustrates a radial dial indicator 111 that presents different parameter values for selection by a user to provide parameter-directed shifting of electrode combinations for a selected program in a current program group.

As an illustration, a user may select the radial dial indicator 111 and then use the increase or decrease buttons 48, 50, or other input media, to cause the arrow to rotate to the desired shift parameter value, e.g., 1, 2 or 3. In response, programmer 20 generates a command to cause stimulator 14 to shift the electrode combination as indicated by the selected shift parameter value.

FIG. 6C illustrates one example of various graphical metaphors that may be used to support shift parameter value adjustment by a user. In general, other possible metaphors should consistently provide a parameter-directed presentation of electrode combination, so that a user may readily enter adjustment of shift parameter values like other parameters, such as program group, program, amplitude, pulse width, pulse rate, and the like.

In the example of FIG. 6C, screen 35C presents an additional icon in the form of exclamation point 95 to indicate a notification or alarm state. Exclamation point 95, or some other alarm indicator such as a blinking icon, question mark, audible tone, vibration, or the like, may be provided when the user attempts to adjust the shift parameter value beyond its maximum or minimum value. If the user actuates an increase button when the shift parameter value is already at a maximum value, e.g., 3 in FIG. 6C, then programmer 20 may present exclamation point 95 as a notification that the user is attempting to shift the electrode combination beyond the maximum distal or proximal position on the lead set. Programmer 20 may present a similar notification when a user attempts to perform shifting while stimulation is off. The notification may ask whether the user wishes to turn on stimulation to affect the desired shift procedure.

Figure 6D:
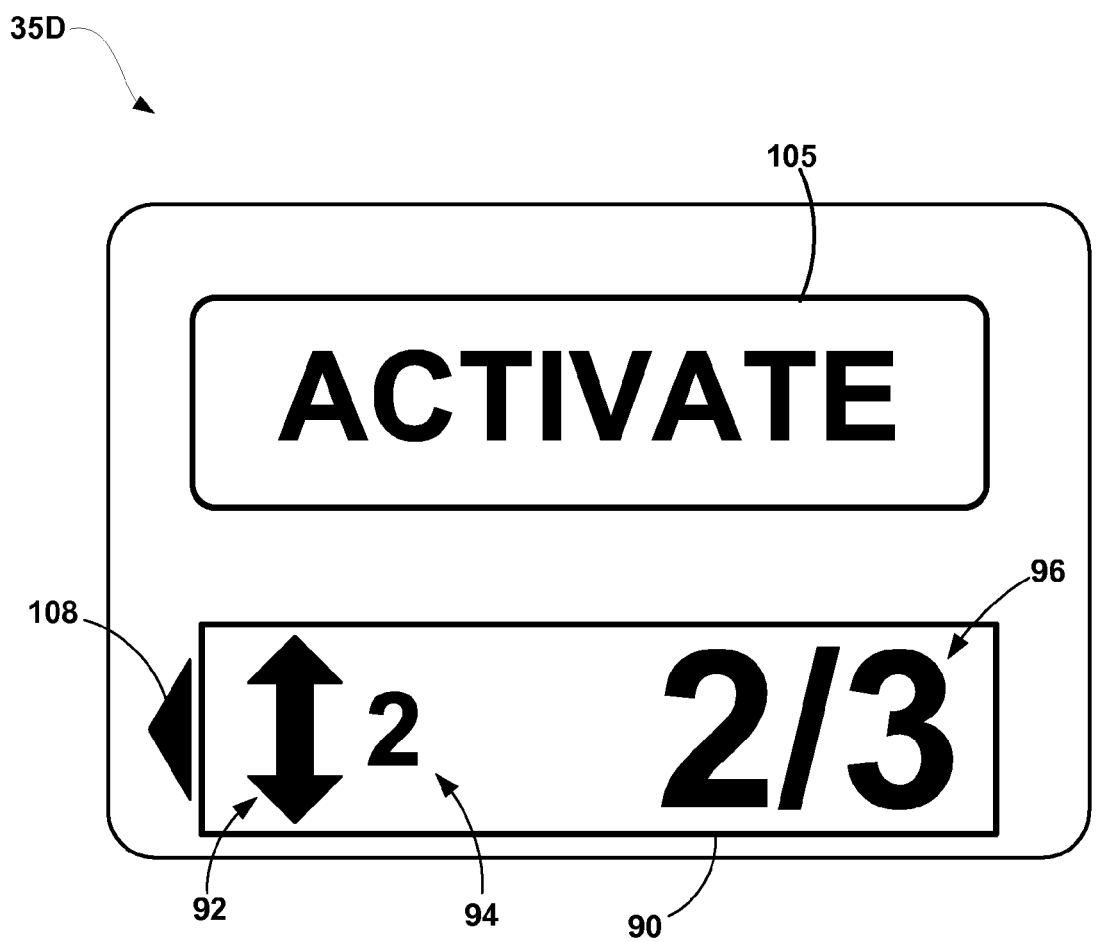
FIG. 6D is a conceptual diagram illustrating an example user interface of an external programmer for receiving parameter-directed input indicating desired shifting of electrode combinations in conjunction with a modal command for activation of the desired shifting.

FIG. 6D is a conceptual diagram illustrating an example user interface of an external programmer 20 for receiving parameter-directed input indicating desired shifting of electrode combinations in conjunction with a modal command for activation of the desired shifting. FIG. 6D conforms substantially to screen 35A of FIG. 6A. However, FIG. 6D shows a screen 35D in which programmer 20 presents a modal activation button 105 to control activation of delivery of stimulation for an indicated shift position of an electrode combination. In the example of FIG. 6D, the user adjusts a shift parameter value 96 as described above. Before activating the desired shift position, however, programmer 20 waits for explicit instruction via modal activation button 105.

Hence, instead of automatically generating a command for stimulator 14 to deliver stimulation via the electrode combination indicated by the shift parameter value, programmer 20 awaits an activate instruction from the user via modal activation button 105. The activate instruction, in some embodiments, may be a sync command that causes programmer 20 to synchronize its state with stimulator 14. In this manner, a user may adjust the shift parameter value 96 multiple times before finally selecting a desired shift parameter value. Instead of having programmer 20 immediately and automatically apply each selected shift parameter value, the user can control when the stimulation is delivered, e.g., by a synch or activation command that synchronizes the then-current state in programmer 20 for delivery to stimulator 14 as a command or set of commands. As an illustration, the user may scroll through shift position 1, then 2, then 3 and then perhaps back to 2, and then decide to actually apply stimulation via the selected electrode combination that corresponds to the shift parameter value.

Figure 7:
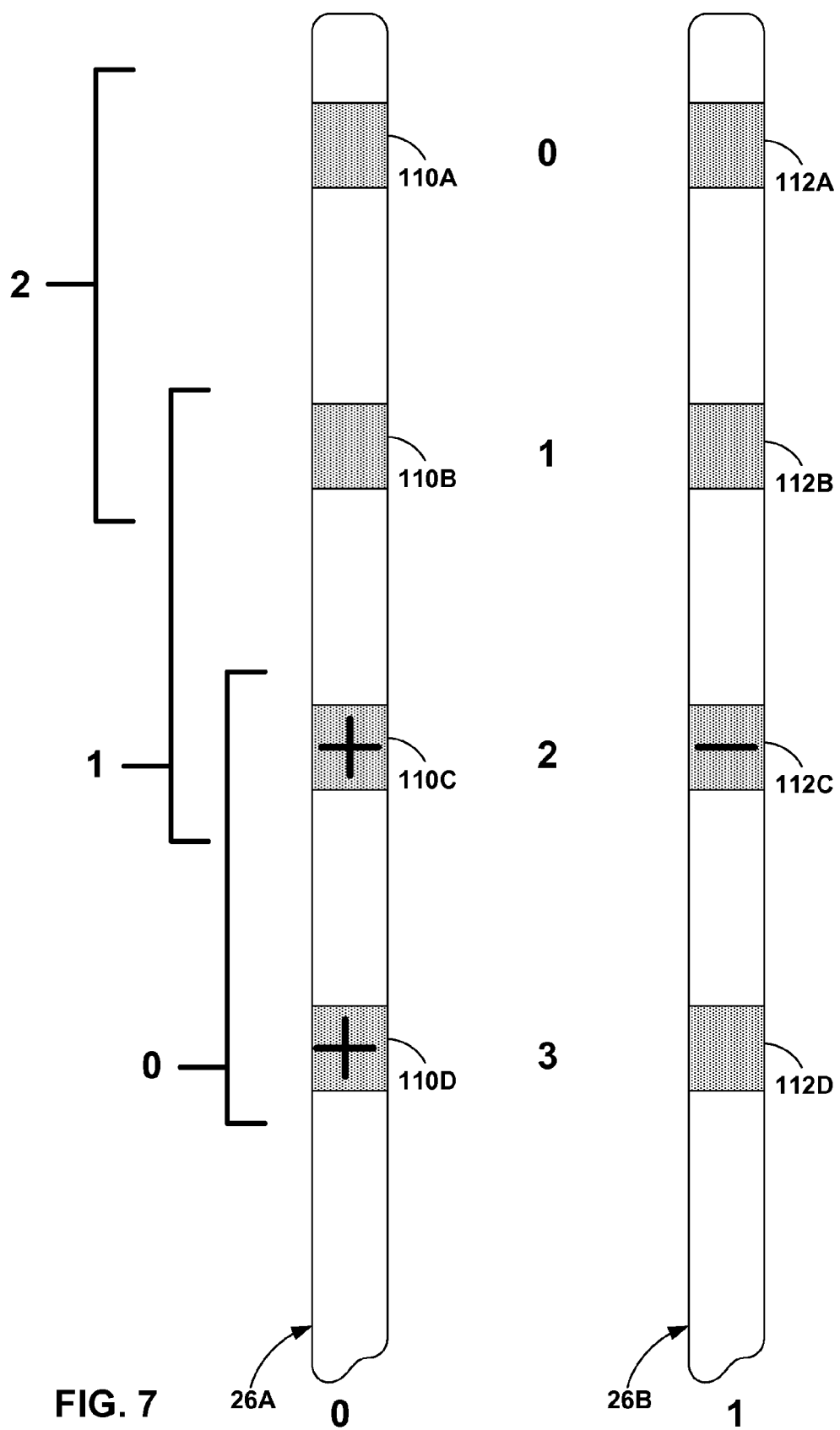
FIG. 7 is a schematic diagram illustrating a pair of leads with the same electrode count, and example shift positions.

FIG. 7 is a schematic diagram illustrating a pair of leads 26A, 26B with the same electrode count, and example shift positions. In the example of FIG. 7, each lead 26 includes four electrodes, i.e., electrodes 110A-110D on lead 26A and 112A-112D on lead 26B. (In other cases, each lead 26 may include a different electrode count, such as eight electrodes on lead 26A and eight electrodes on lead 26B.) Each lead 26 includes four electrode levels, 0 through 3, as indicated in FIG. 7. If an electrode combination includes positive electrodes 110C and 110D (at levels 2 and 3) on lead 26A and a negative electrode 112C (at level 2) on lead 26B, i.e., an electrode lead combination of (3+/0, 2+/0, 2−/1), then the electrode combination cannot be shifted proximally, i.e., down in the orientation of FIG. 7, because electrode 110D at level 3 is already the most proximal electrode on lead 26A.

However, the electrode combination can be shifted distally, i.e., upward in the orientation of FIG. 7. There is room on leads 26A, 26B to shift the electrode combination distally by two shift positions. Hence, if the initial position is shift position 1, shifts can be made to shift position 2 and shift position 3. Each shift may represent a shift in the position of the active electrodes associated with the previous electrode combination such that the electrical stimulation pattern remains identical or substantially similar, e.g., in terms of relative positions and spacing between the active electrodes in both the initial and shifted electrode combination. In addition, the initial and shifted electrode combinations have a common number of electrodes. In the example of FIG. 7, each electrode combination has three electrodes (110C, 110D, and 112C for the first combination), and the electrode combinations have a substantially similar electrode pattern. Active electrodes are those electrodes actually selected for delivery of electrical stimulation. Designating lead 26A as lead 0 and lead 26B as lead 1, and designating electrodes 110A-110D and 112A-112D as electrode levels 0-3, respectively, the possible shift positions for the lead set of FIG. 7 are shift position 1 (0/0, 1/0, 1/1), shift position 2 (1/0, 2/0, 2/1) and shift position 3 (2/0, 3/0, 3/1), each of which may correspond to a shift parameter value, e.g., 1/3, 2/3 or 3/3. Given the electrode combination in FIG. 7, it is not possible to shift the electrical stimulation pattern below shift position 1 or above shift position 3, which represent the maximum boundaries of the shift range, yielding three shift positions for selection by the user via parameter-directed shifting.

Figure 8:
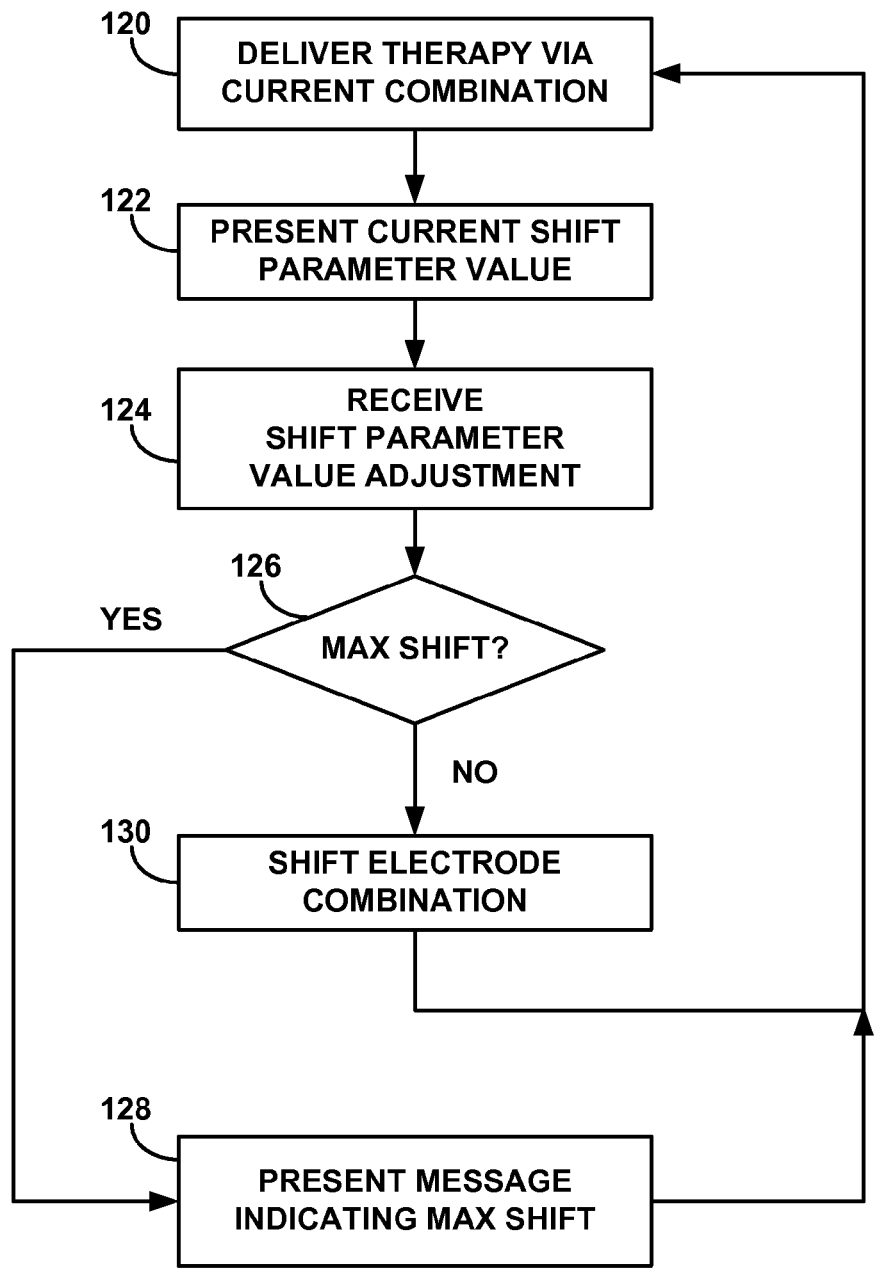
FIG. 8 is a flow diagram illustrating a technique for parameter-directed shifting of electrode combinations along the pair of leads of FIG. 7.

FIG. 8 is a flow diagram illustrating a technique for parameter-directed shifting of electrode combinations along the pair of leads of FIG. 7. As shown in FIG. 8, programmer 20 causes stimulator 14 to delivery therapy via a current electrode combination (120) and presents the current shift parameter value to the user (122), e.g., via one of the screens illustrated in FIGS. 6A-6D. Upon receiving a shift parameter value adjustment (124), e.g., by adjustment of a parameter value or selection of a parameter value, programmer 20 determines whether the resulting shift would extend beyond the maximum boundaries of the shift range (126). If so, programmer 20 presents a message, alarm or other notification, such as exclamation point 95 of FIG. 6C or some audible tone, vibration or the like, indicating one of the maximum boundaries of the shift range has been reached (128). If not, programmer 20 generates a command to cause stimulator 14 to shift the electrode combination (130). The shifted electrode combination may generally conform to the previous electrode combination, e.g., in terms of relative position and spacing of active electrodes in the electrode combination, but be shifted by one or more positions axially in a selected direction along the length of the lead.

In some examples, a resulting shift that would extend beyond the maximum boundaries of the shift range, e.g., 3/3 or 1/3, may not result in a notification to the user. Instead, the next shift in electrode combination may automatically cycle back to the opposite end of the lead. In other words, a shift that would extend beyond the distal end of the possible electrode combinations may directly go to the most proximal electrode combination. In alternative examples, the shift may not need to reach the maximum boundary before presenting the user with a notification or forcing the next shift to the opposite end of the leads. If the user does not regularly use shift positions toward the maximum boundary, has blocked out shift positions toward the maximum boundary, or shift positions are recognized by stimulator 14 or programmer 20 as not appropriate for stimulation, programmer 20 may directly notify the user or shift the position to the opposite end of the leads.

Figure 9:
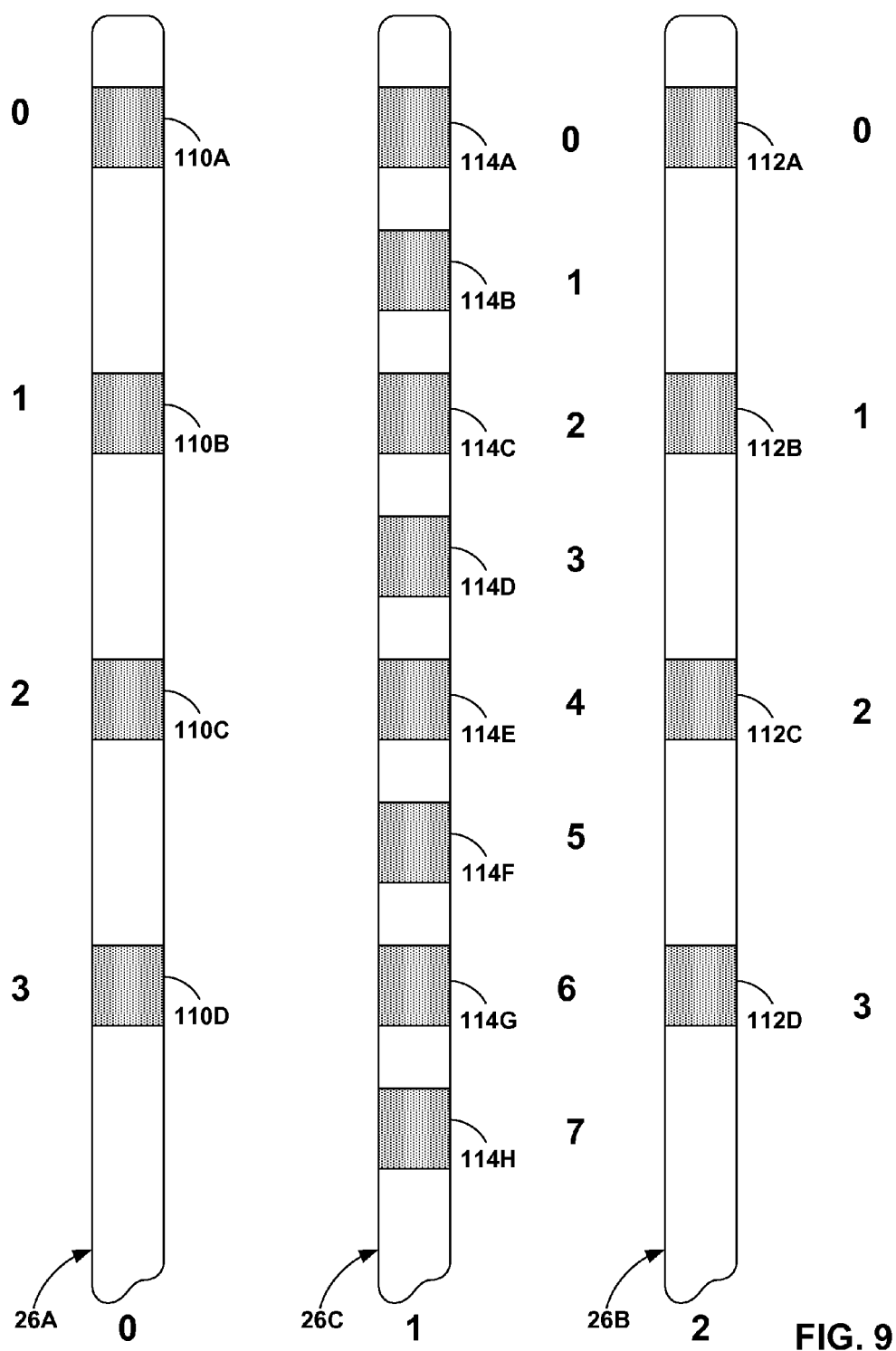
FIG. 9 is a schematic diagram illustrating a trio of leads with different electrode counts.
Figure 10:
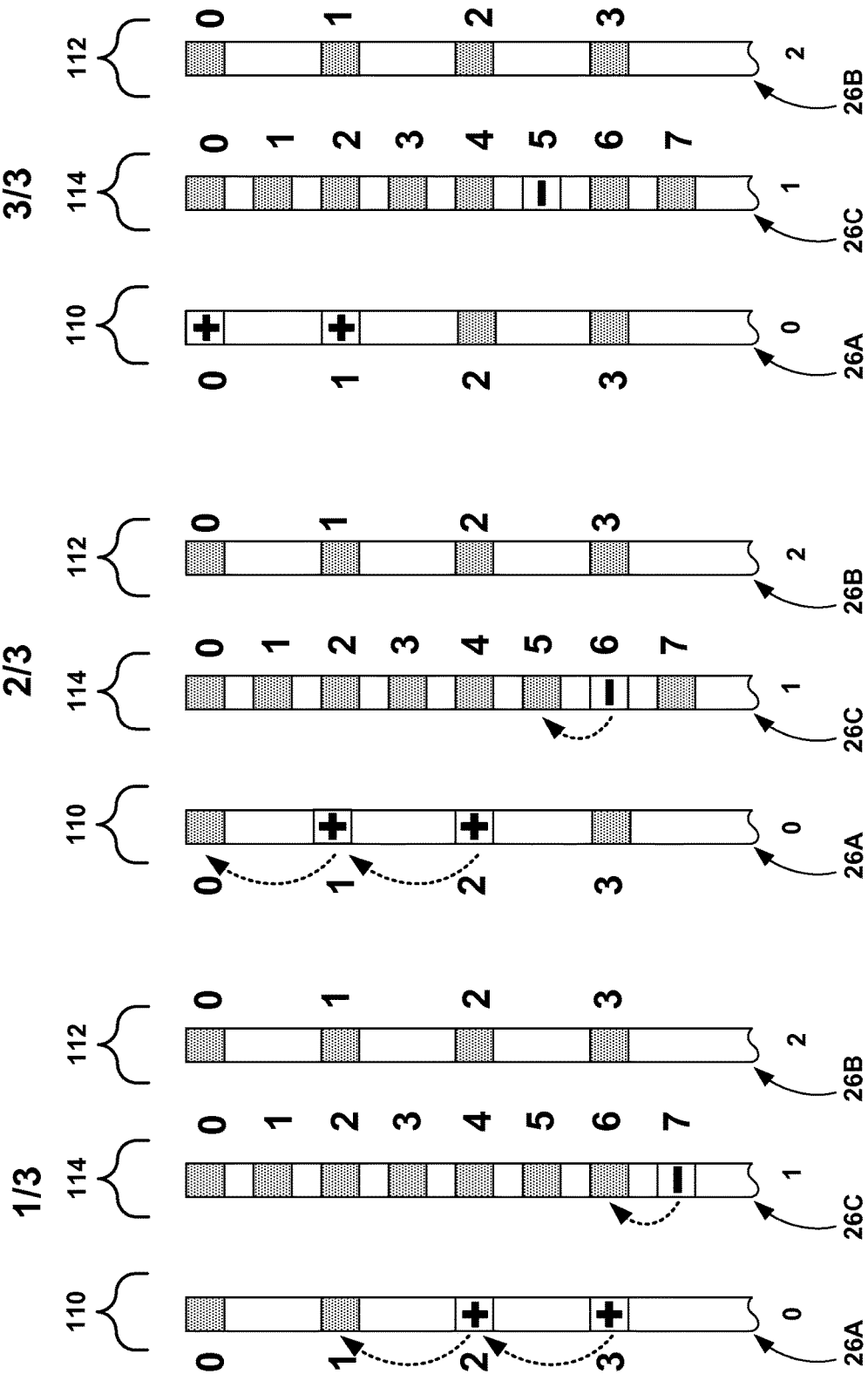
FIGS. 10A-10C are schematic diagrams illustrating a technique for parameter-directed shifting of electrode combinations among a trio of leads with different electrode counts.
Figure 11:
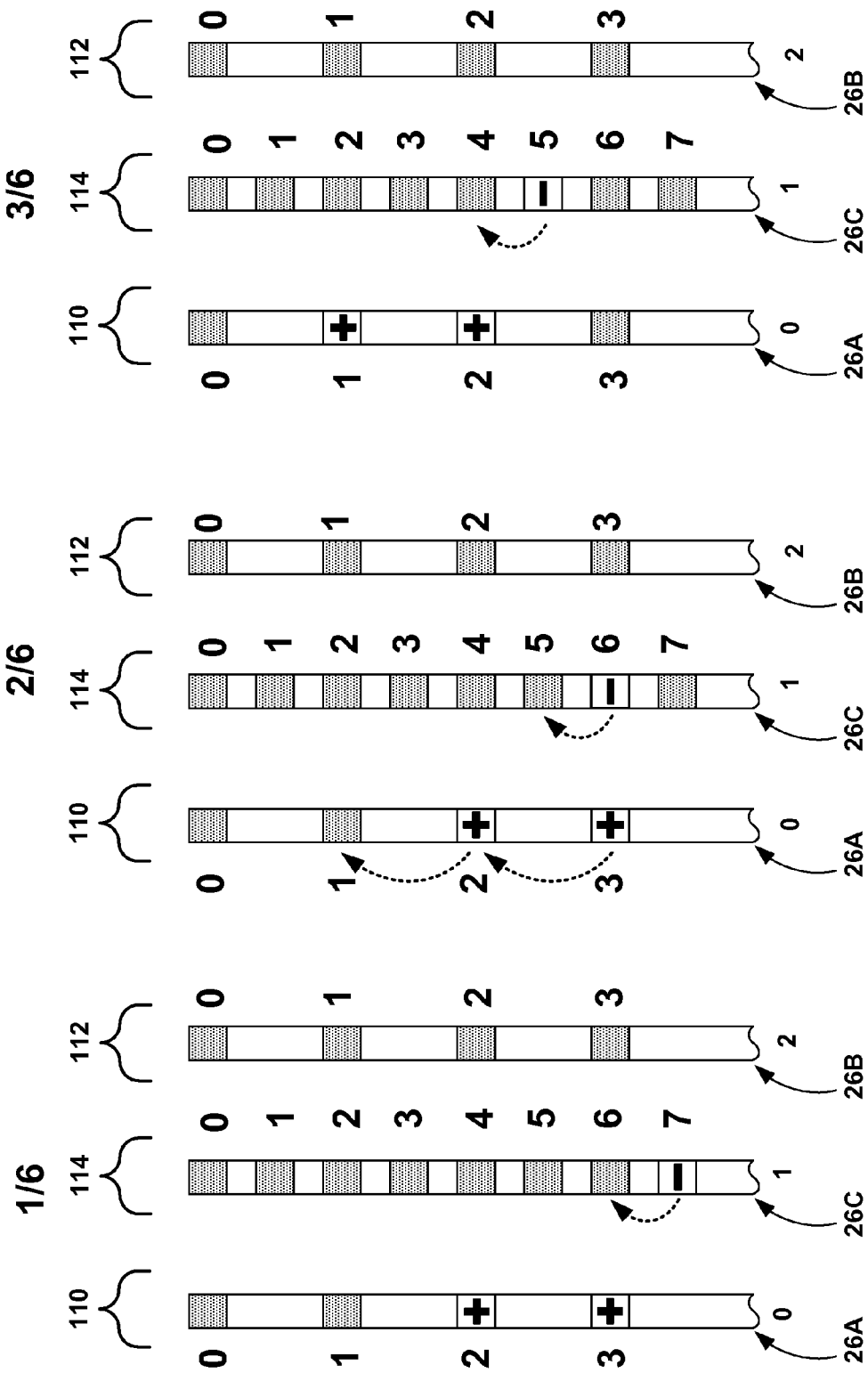
FIGS. 11A-11C are schematic diagrams illustrating another technique for parameter-directed shifting of electrode combinations among a trio of leads with different electrode counts in a first direction along the leads.
Figure 12:
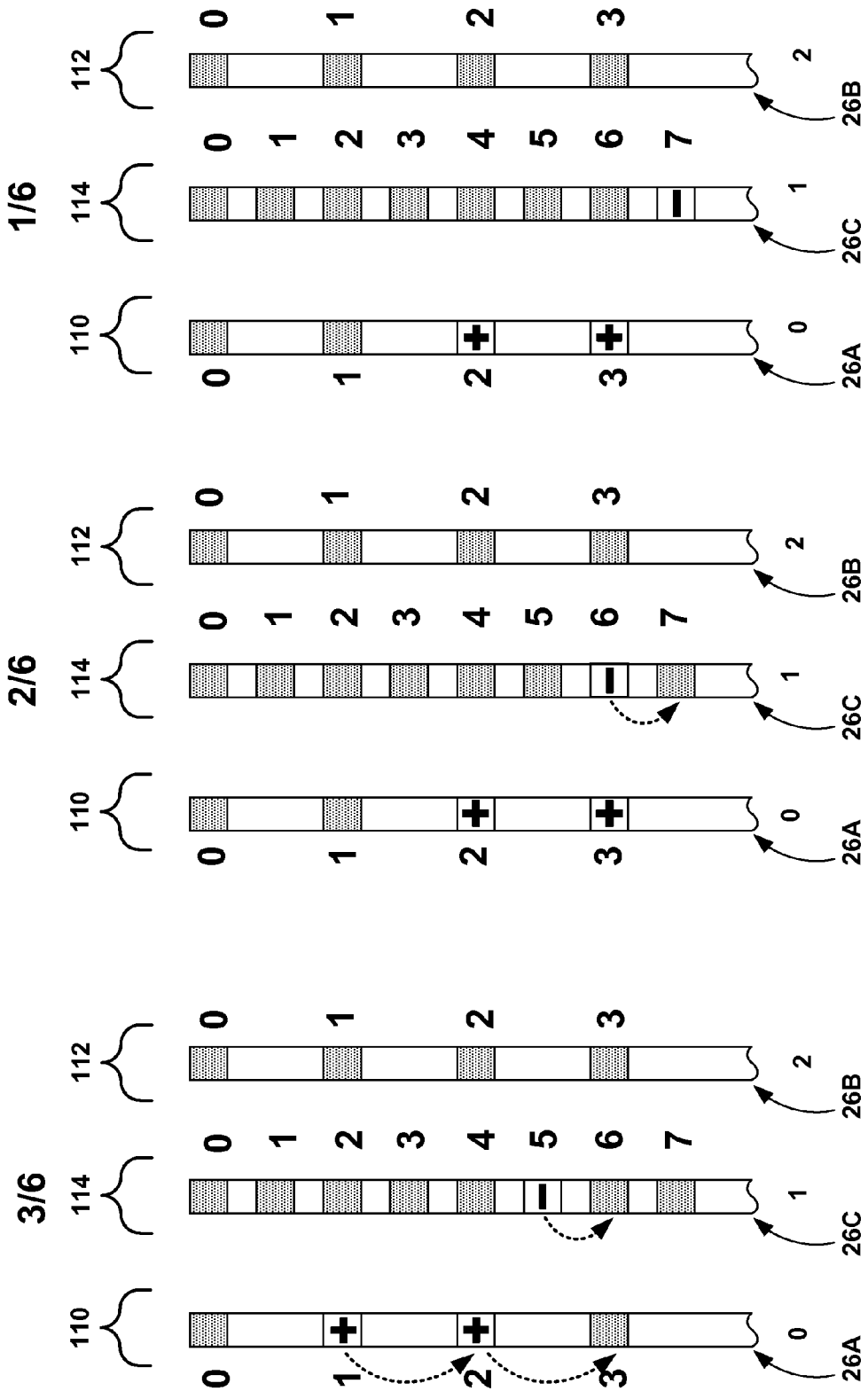
FIGS. 12A-12C are additional schematic diagrams illustrating another technique for parameter-directed shifting of electrode combinations among a trio of leads with different electrode counts in a second direction along the leads.

FIG. 9 is a schematic diagram illustrating a trio of leads 26A, 26B, 26C with different electrode counts. In the example of FIG. 9, leads 26A, 26B each include four electrodes (110A-110D and 112A-112D) while lead 26C includes eight electrodes (114A-114H). In the example of FIG. 9, the adjacent implantable leads 26A-26C may have longitudinal axes that are substantially parallel to one another. The lead configuration of FIG. 9 may be referred to as a 4-8-4 configuration in the sense that leads 26A, 26C, 26B have four, eight, and four electrodes, respectively. Other electrode configurations, such as 4-8, 8-4, 8-16, 2-4, 2-8, 2-16, 4-16-4, 8-16-8, 8-4-8, 16-8-16, 8-2-4, or the like, are possible. The use of leads with different electrode counts may be desirable in various therapeutic applications, but creates an issue for purposes of electrode shifting. In particular, for every electrode shift on one lead, there may be multiple electrode shifts on another lead. In FIG. 9, for every single shift on leads 26A, 26B, there are two shifts possible on lead 26C.

In accordance with an embodiment of this disclosure, an electrode combination shifting technique may involve executing shifts in steps, where the number of shift steps along the length of a lead having a greater electrode count is greater than the number of shift steps along the length of a lead having a lesser electrode count. With reference to FIG. 9, for example, every shift step on leads 26A, 26B may correspond to two shift steps on lead 26C. As an illustration, if leads 26A, 26C, and 26B are designated leads 0, 1 and 2, respectively, and if an electrode combination initially comprises electrode 1 on lead 0, electrode 2 on lead 1 and electrode 1 on lead 2 (1/0, 2/1, 1/2), then shifting along the lead set may be divided among sub-steps along lead 1.

FIGS. 10A-10C are schematic diagrams further illustrating a technique for parameter-directed shifting of electrode combinations among a trio of leads 26A-26C with different electrode counts. In particular, FIGS. 10A-10C illustrate problems in shifting electrodes one position at a time when the leads have different electrode counts. If the parameter-directed shifting technique moves the electrode combination up or down by one electrode level for every shift step, then the 4-electrode leads would reach the top or bottom of the lead set very quickly, while the 8-electrode lead would not fully traverse the electrode levels along the lead length. As shown in FIG. 10A, at a first position (1/3), the electrode combination includes two positive electrodes (anodes) on lead 0 at levels 2 and 3, and one negative electrode (cathode) on lead 1 at level 7, i.e., an electrode/lead combination of (2+/0, 3+/0, 7−/1).

If the electrode combination is shifted distally one position, as indicated by the arrows in FIG. 10A, the result is shown in FIG. 10B as (1+/0, 2+/0, 6−/1). Hence, in the second position (2/3), the positive electrodes are at levels 1 and 2, and the negative electrode is at level 6. In this example, increases in the shift parameter value, e.g., from 1/3 to 2/3, indicate movement in a proximal-to-distal direction. From example, as indicated in FIGS. 10A and 10B, the increase in the shift parameter value from 1/3 to 2/3 results in a change in the electrode combination from (2+/0, 3+/0, 7−/1) to (1+/0, 2+/0, 6−/1). As mentioned previously, however, an opposite shift parameter value orientation could be used, depending on design considerations, such that increases in shift parameter value indicate shifts in the opposite direction, i.e., distal to proximal.

Notably, the positive electrodes have been moved a greater distance distally than the negative electrode, because lead 0 has only four electrode levels whereas lead 1 has eight electrode levels. Hence, there is a mismatch in the distance traveled on the different leads in successive shift steps, resulting in a change in the pattern or shape of the electrode combination in terms of the distances between electrodes on the 4-count leads and electrodes on the 8-count lead. In particular, the relative positions and spacing between active electrodes changes, resulting in a change in the stimulation pattern. This change is even more pronounced in the next shifting step, shown in FIG. 10C. In particular, at shift position 3/3, the positive electrodes on lead 0 are at electrode levels 0 and 1, but the negative electrode on lead 1 is at electrode level 5. A substantial change in the shape of the electrode combination as a result of the parameter-directed switching process may be undesirable in some applications. To better preserve the electrical stimulation pattern, in terms of the relative spacing and positions of the electrodes in the electrode combination in the example of FIGS. 10A-10C, the parameter-directed shifting technique can be modified to move one electrode level on the 4-electrode leads for every two electrode levels traversed on the 8-electrode lead, as will be described in greater detail below.

FIGS. 11A-11C are schematic diagrams illustrating another technique for parameter-directed shifting of electrode combinations among a trio of leads with different electrode counts in a first direction along the leads. FIGS. 12A-12C are additional schematic diagrams illustrating this technique for parameter-directed shifting of electrode combinations among a trio of leads with different electrode counts in a second direction along the leads. In the examples of FIGS. 11A-11C and 12A-12C, the parameter-directed shifting process applies a modified shifting sequence to better retain the shape and relative spacing of the electrical stimulation pattern delivery via the electrode combination as it is shifted up or down, i.e., distally or proximally, along the length of the lead set. Instead of shifting each electrode one step for each shift position, additional shift positions are provided to accommodate intermediate shifting steps on a lead with a greater number of electrodes than other leads.

FIGS. 11A-11C illustrate upward shifting on leads 0, 1, 2, i.e., in a direction from a proximal toward a distal end, starting with an initial electrode/lead combination of 2+/0, 3+/0, 7−, 1). Programmer 20 may apply a general rule for upward shifting to shift either an electrode(s) on the 8-count lead alone or to shift both the electrode(s) on the 8-count lead and the electrode(s) on the 4-count leads. In particular, if the most proximal active electrode on the 8-count lead is an odd number, e.g., 1, 3, 5, or 7, then programmer 20 shifts only the active electrode on the 8-count lead in accordance with an upward shifting rule. However, if the most proximal active electrode on the 8-count lead is an even number, e.g., 0, 2, 4, or 6, then programmer 20 shifts the active electrode on the 8-count lead and any active electrodes on the 4-count leads per the upward shifting rule.

In response to user input selecting a shift parameter value that results in a single level shift in the upward direction (proximal to distal), programmer 20 causes stimulator 14 to move stimulation from the electrode/lead combination of (3+/0, 2+/0, 7−/1) to the combination of (3+/0, 2+/0, 6−/1), as illustrated in FIG. 11A, because the most proximal active electrode on the 8-count lead was electrode 7, an odd-numbered electrode. In the example of FIGS. 11A-11C, there are six possible shift positions, bounded by maximum distal and proximal boundaries. The first shift step moves the electrode combination from shift parameter 1/6 to shift parameter 2/6.

In a second shift step, in response to user input specifying another shift parameter value that results in another single level shift, stimulator 14 moves both the electrodes on the 4-count lead 0 and the electrode on the 8-count lead 1. In this case, the most proximal active electrode on the 8-count lead was electrode 6, an even-numbered electrode. In the second shift step, programmer 20 causes stimulator 14 to move the electrode combination from (3+/0, 2+/0, 6−/1) to (2+/0, 1+/0, 5−, 1), as shown in FIG. 11B. In a third shift step, the electrode combination moves from (2+/0, 1+/0, 5−, 1) to (2+/0, 1+/0, 4−, 1). As shown in FIG. 11C, the third shift step moves the negative active electrode on the 8-count lead, but does not move the positive electrodes on the 4-count lead 0, because the active electrode on the 8-count lead is at odd-numbered position 5.

In general, using an upward shifting rule as outlined above, the electrode level on the 8-count lead 1 is shifted one level, but the electrode levels on the 4-count lead 0 are maintained at their existing positions for odd numbered starting positions for the most proximal active electrode on the 8-count lead. For even-numbered starting positions for the most proximal active electrode on the 8-count lead, all active electrodes on all leads are shifted. As a result of the process shown in FIGS. 11A-11C, every other shift step (i.e., on an alternating basis) will produce an electrode combination with an electrode pattern that is substantially identical to the original electrode combination, albeit shifted. Intermediate shift steps will produce an electrode combination that is not identical, but provides a reasonable approximation of the original electrode combination. In general, the electrode level on the 8-count lead 1 is shifted one level, but the electrode levels on the 4-count lead 0 are maintained at their existing positions.

With further reference to FIGS. 11A-11C, electrodes are shifted for every step on the 8-count lead, but only every other step on the 4-count lead, i.e., on an alternating basis. In this manner, the parameter-directed shifting technique may at least partially preserve the shape of the electrical stimulation pattern delivered via the electrode combination as it is shifted up or down the lead, as mentioned above. In general, the electrode or electrodes on lesser count lead(s) are moved one step for every two steps on the greater count lead, e.g., in the case of 2 count versus 4 count leads, 4 count versus 8 count leads, or 8 count versus 16 count leads. If different count ratios apply, then different stepping rules may apply. If there is a 4 electrode lead and a sixteen electrode lead, for example, then the electrodes on the 4-count lead could be shifted once for every four shifts on the 16-count lead.

This shifting process may be performed by stimulation generator 62 of stimulator 14 in response to control instructions from processor 58. For example, stimulation generator 62 may control switching circuitry to apply electrical stimulation via different electrode combinations on implantable leads 16. In turn, processor 58 may be responsive to one or more shift commands generated by programmer 20 in response to patient input, and transmitted via wireless telemetry. For example, processor 58 may be responsive to perform a series of shift operations in response to a single shift command from programmer 20. Alternatively, processor 58 may be responsive to a series of shift commands from programmer 20 that drive individual shift operations in a series of shift operations.

The upward and downward shifting rules may be applied by programmer 20 or stimulator 14. For example, programmer 20 may generate commands that specify each step in the shifting operation, including each step according to the applicable rule. In particular, for an upward shift, programmer 20 may apply the upward or downward shifting rule to specify whether all active electrodes should be shifted or just the active electrode(s) on the larger-count lead should be shifted. In this case, programmer 20 may send a separate command for each shift step. As an alternative, programmer 20 may simply generate a command that indicates the desired shift position, consistent with the shift parameter value. In this case, stimulator 14 may be responsible for determining the individual steps according to the upward or downward shifting rule, as applicable. Hence, the intelligence for applying the shifting rules may be provided in programmer 20 or stimulator 14.

FIGS. 12A-12C illustrate downward shifting on leads 0, 1, 2, i.e., in a direction from a distal toward a proximal end, starting with an initial electrode/lead combination of (1+/0, 2+/0, 5−, 1). The basic rule outlined above for upward movement with respect to FIGS. 11A-11C may not be appropriate for traversing the lead set in the opposite, downward direction. Instead, programmer 20 may apply a different rule to handle user input selecting a shift parameter value that results in a single level shift in the downward (distal to proximal) direction. The shifting rule for downward shifting may be similar to, but slightly different from, the rule applied for upward shifting in FIGS. 11A-11C.

In general, the downward shifting rule may be formulated as follows. If the user adjusts the shift parameter value to a value that indicates a downward shift, then programmer 20 causes stimulator 14 to shift all electrodes in the electrode combination if the most proximal active electrode on the lead with the greater electrode count is an odd-numbered electrode, e.g., 1, 3, 5, or 7. Alternatively, if the most proximal active electrode on the lead with the greater electrode count is not odd-numbered, then programmer 20 causes stimulator 14 to shift only the electrode(s) on the lead with the greater electrode count. With separate rules for upward and downward movement, programmer 20 may better preserve the shape of the electrical stimulation pattern produced by the electrode combination as it is shifted up and down the lengths of the leads. In particular, the relative spacing between electrodes may be better preserved between different electrode combinations. Alternating shift steps may result in a substantially identical stimulation pattern, while other shift steps may result in slight differences in the stimulation pattern.

Applying the downward shifting rule, if the first electrode combination is (1+/0, 2+/0, 5−, 1), corresponding to shift parameter value 3/6, as shown in FIG. 12A, programmer 20 executes a first downward shifting step by causing stimulator 14 to shift all active electrodes, resulting in an electrode combination of (2+/0, 1+/0, 6−/1), corresponding to shift parameter value 2/6. In this case, the most proximal active electrode on the 8-count lead was positioned at an odd position, i.e., position 5. On this basis, application of the downward shifting rule to the initial electrode combination of FIG. 12A results in shifting all electrodes down one position. For the resulting electrode combination, programmer 20 applies the downward shifting rule to shift only the negative electrode on the eight-count lead in the second shifting step. In this case, the most proximal active electrode on the eight-count lead is even-numbered, so only that electrode is shifted. The result of the shift is the electrode combination (2+/0, 3+/0, 7−/1), as indicated in FIG. 12B.

In FIG. 12C, there is no further downward shift, even if requested by a user via a shift parameter value adjustment, because the electrode combination has reached the maximum proximal bound of the shifting range. Programmer 20 may advise the user that no further downward shifting is possible for the current electrode combination. This fact may be indicated by a notification, visual, audible or otherwise, or simply by indicating that the current shift parameter value is 1/6, i.e., the lowest possible parameter value. Similarly, a parameter value of 6/6 would indicate the maximum distal boundary for the shifting range. Yet, neither 1/6 nor 6/6 explicitly or directly provides an indication of position. Rather, patient 12 or another user may simply view the designation 1/6 or 6/6 as another parameter value, much like other parameter values that can be adjusted by the user.

Set forth below is a set of upward and downward shifting rules that may be used to govern shifting for the example scenario in which one lead is an 8-count (1×8) lead and at least one other lead is a 4-count (1×4) lead:

A. If all of the following are true: 1) a program has active electrodes on a 1×8 lead and a 1×4 lead, 2) the most proximal active electrode on the 1×8 lead is on the 1st, 3rd, 5th, or 7th electrode available on the 1×8 lead (with the electrodes numbered 0 to 7 from the distal to the proximal end of the leads in FIGS. 12A-12C), and 3) the user selects increase for the shift parameter value (indicating upward movement toward the distal end), then the programmer 20 shall shift the electrode combination on the 1×8 lead only.

B. If all of the following are true: 1) a program has active electrodes on a 1×8 lead and a 1×4 lead, 2) the most proximal active electrode on the 1×8 lead is on the 0th, $2^{nd}$, 4th, or 6th electrode available on the 1×8 lead (with the electrodes numbered 0 to 7 from the distal to the proximal end of the leads in FIGS. 12A-12C), and 3) the user selects increase for the shift parameter value (indicating upward movement toward the distal end), then the programmer 20 shall shift all electrodes in the program.

C. If all of the following are true: 1) a program has active electrodes on a 1×8 lead and a 1×4 lead, 2) the most proximal active electrode on the 1×8 lead is on the 1st, 3rd, 5th, or 7th electrode available on the 1×8 lead (with the electrodes numbered 0 to 7 from the distal to the proximal end of the leads in FIGS. 12A-12C), and 3) the user selects decrease for the shift parameter value (indicating downward movement toward the proximal end), then the programmer 20 shall shift all electrodes in the program.

D. If all of the following are true: 1) a program has active electrodes on a 1×8 lead and a 1×4 lead, 2) the most proximal active electrode on the 1×8 lead is on the 0th, $2^{nd}$, 4th, or 6th electrode available on the 1×8 lead (with the electrodes numbered 0 to 7 from the distal to the proximal end of the leads in FIGS. 12A-12C), and 3) the user selects decrease for the shift parameter value (indicating downward movement toward the proximal end), then the programmer 20 shall shift the electrode combination on the 1×8 lead only.

Figure 13:
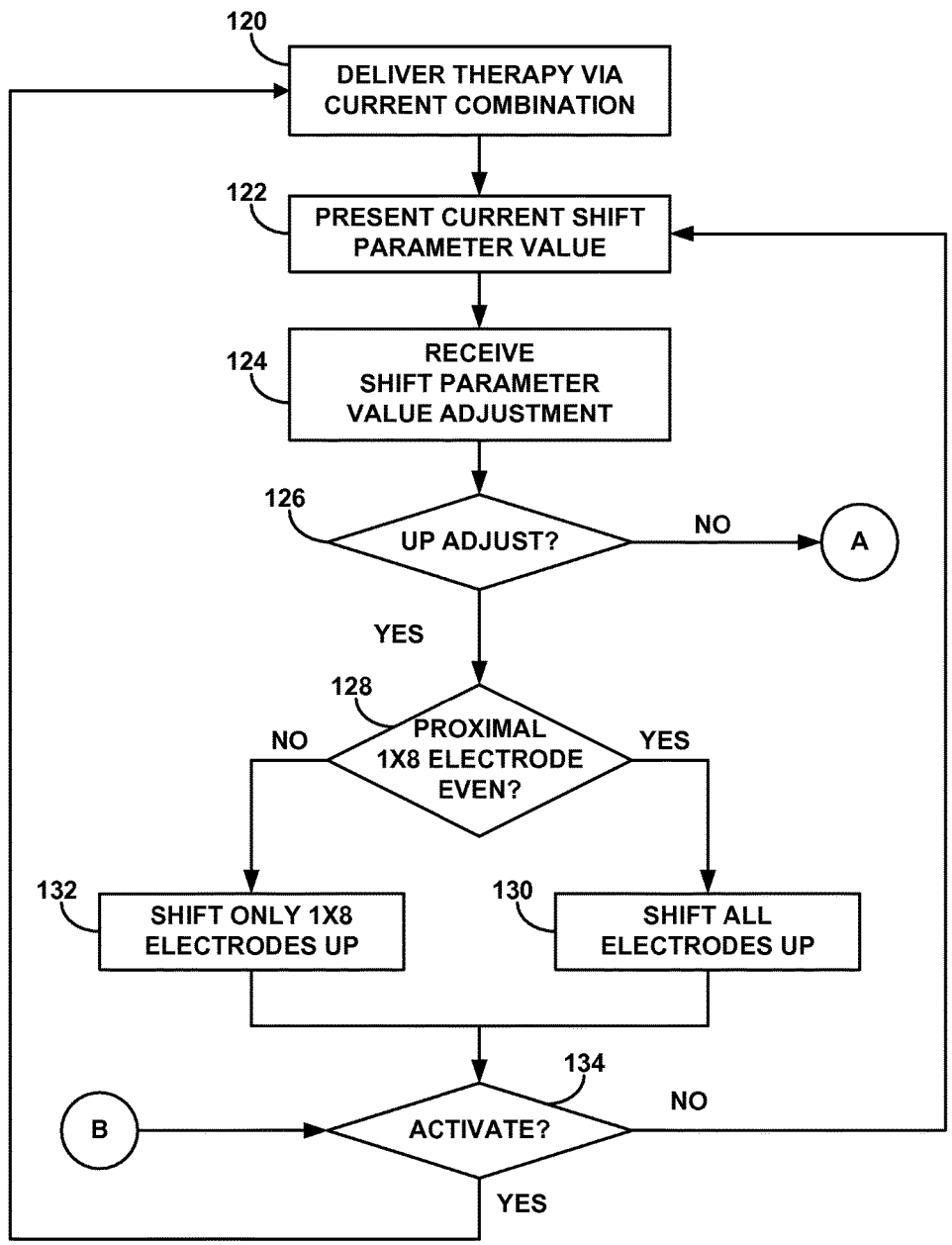
FIG. 13 is a flow diagram illustrating a technique for parameter-directed shifting of electrode combinations in a first direction among leads with different electrode counts.

FIG. 13 is a flow diagram illustrating a technique for parameter-directed shifting of electrode combinations in a first direction among leads with different electrode counts. In the example of FIG. 13, programmer 20 may apply the upward shift rule described above to achieve parameter-directed shifting of electrode combinations in a proximal-to-distal direction along the length of a lead set. As shown in FIG. 13, stimulator 14 may deliver stimulation therapy to patient 12 via a current electrode combination (120). Programmer 20 presents the current shift parameter value to the user (122), either full-time or upon navigation to a screen associated with or dedicated to adjustment of the shift parameter value for a given program.

Figure 14:
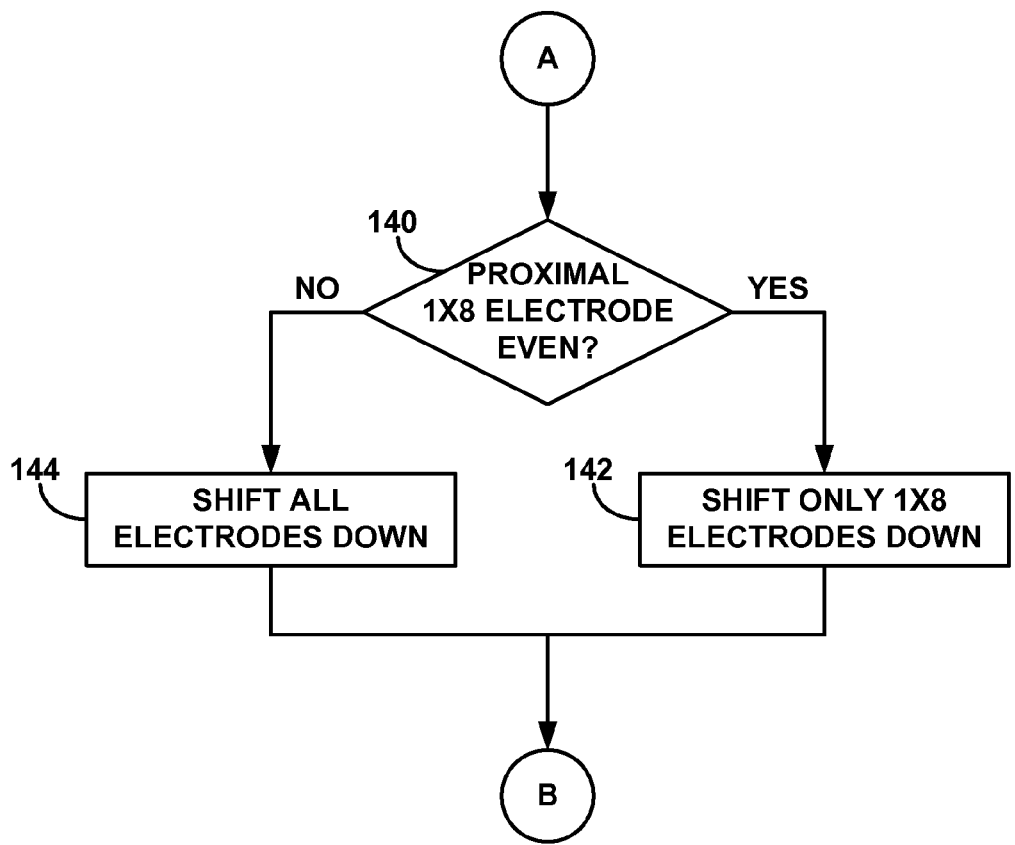
FIG. 14 is another flow diagram illustrating a technique for parameter-directed shifting of electrode combinations in a second direction among leads with different electrode counts.

Upon receiving a shift parameter value adjustment (124) from the user, programmer 20 determines whether the adjustment results in an upward (proximal-to-distal) shift or a downward (distal-to-proximal) shift (126). If the shift parameter value adjustment is downward, programmer 20 applies downward shift rules and follows branch A, which is illustrated in FIG. 14. If the shift parameter adjustment is upward, programmer 20 applies the upward shift rule. In particular, programmer 20 determines whether the most proximal active electrode on the 1×8 lead is even numbered (128), e.g., 0, 2, 4, 6 numbered from distal to proximal. If the most proximal active electrode is even, programmer 20 shifts all electrodes up by one position (130). If the most proximal electrode is not even, programmer 20 shifts only the active electrode(s) up by one position on the 1×8 lead (132).

The electrode combination resulting from the shift may be activated automatically by programmer 20. For example, programmer 20 may ramp down the stimulation amplitude on the previous electrode combination and ramp up the stimulation amplitude on the shifted electrode combination. The ramp process may be gradual and may ramp down to zero and upward to a target level. The target level may be the same for both the previous and target electrode combinations, or different depending on differing impedance and sensitivity levels measured or assumed for the respective electrode combinations.

As an alternative to automatically shifting stimulation, programmer 20 may wait for the patient 12 or other user to indicate activation (134), e.g., by selecting an activate button as in the example of FIG. 6D. If the user does not select the activate button (134), programmer 20 may wait for additional adjustments to the shift parameter value (122, 124). In this case, programmer 20 may permit a user to shift more than one position before actually activating stimulation. When user selects the activate button (134), programmer 20 generates a command to cause stimulator 14 to deliver stimulation therapy via the shifted combination, which becomes the current combination (120).

FIG. 14 is another flow diagram illustrating a technique for parameter-directed shifting of electrode combinations in a second direction among leads with different electrode counts. In particular, FIG. 14 illustrates application of a downward shift rule by programmer 20. As shown in FIG. 14, if the most proximal active electrode on the 1×8 lead is even (140), then programmer 20 shifts only the active electrode(s) on the 1×8 lead in a downward direction (142). If the most proximal active electrode on the 1×8 lead is not even (152), however, programmer 20 shifts all active electrodes on the 1×8 and 1×4 leads down in a downward direction (144). Programmer 20 then may return, via branch B, to wait for input from patient 12 or another user to activate therapy via the current combination. At this point, the process continues as outlined in FIG. 13.

As described with reference to FIGS. 13 and 14, and elsewhere, stimulator 14 delivers electrical stimulation via an electrode combination comprising an electrode in a first implantable array and an electrode in a second implantable array. The implantable arrays of electrodes may be carried by a first implantable lead and second implantable lead. Additionally, in some cases, three or more leads may be used. In the example of FIGS. 13 and 14, at least a second array of electrodes includes a greater number of electrodes than the first array. For example, one lead may include eight electrodes whereas another lead may include only four electrodes. Moreover, a third lead may also have four electrodes, creating a 4-8-4 lead configuration.

To accommodate lead configurations with different lead counts, stimulator 14 may be configured to shift electrical stimulation to different electrode combinations in a series of shift operations, wherein one of the shift operations includes shifting the electrode in the second array while maintaining the electrode in the first array relative to a previous electrode combination. In addition, another of the shift operations includes shifting the electrode in the second array and shifting the electrode in the first array relative to a previous electrode combination. In some embodiments, such shift operations may be performed on a substantially alternating basis, e.g., as described with respect to the upward and downward shift rule examples above.

Figure 15A:
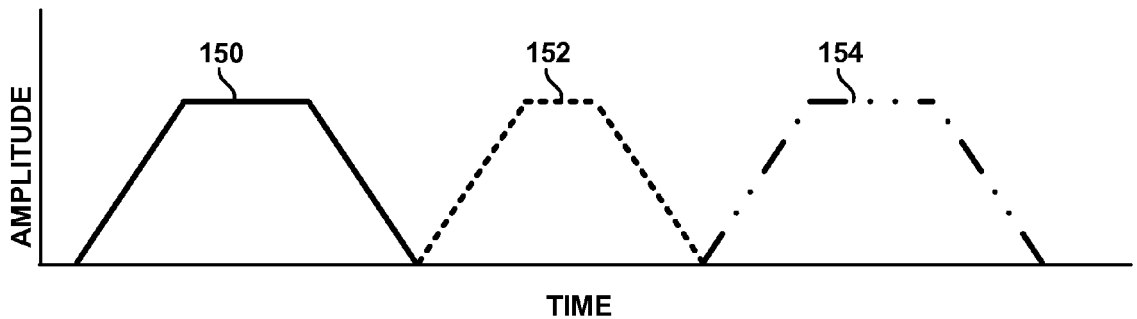
FIG. 15A is a graph illustrating discrete shifting of electrical stimulation between different electrode combinations.

FIG. 15A is a graph illustrating discrete shifting of electrical stimulation between different electrode combinations. Discrete shifting generally refers to a process in which programmer 20 generates commands to cause stimulator 14 to terminate stimulation completely to zero or some minimum level for an initial electrode combination (such as, for example, by immediately terminating or ramping down stimulation) before starting to ramp up stimulation amplitude for a shifted electrode combination. As shown in FIG. 15A, stimulation amplitude 150 for a first electrode combination is ramped up from zero to a target level by stimulator 14. In response to user input specifying a shift parameter adjustment, programmer 20 causes stimulator 14 to ramp stimulation amplitude 150 for the first electrode combination down to zero.

Once zero or some minimum level is reached, programmer 20 causes stimulator 14 to ramp stimulation amplitude 152 up for a second electrode combination. Alternatively, stimulator 14 may automatically ramp down and ramp up stimulation amplitude when a shift indication is received from programmer 20. Upon receipt of another shift parameter adjustment, programmer 20 causes stimulator 14 to ramp down stimulation amplitude 152. Then, upon reaching zero or some minimum level, programmer 20 causes stimulator 14 to start (or stimulator 14 automatically starts) ramping up stimulation amplitude 154 on a third, shifted electrode combination. The process may continue in a similar manner for each newly shifted electrode combination.

Figure 15B:
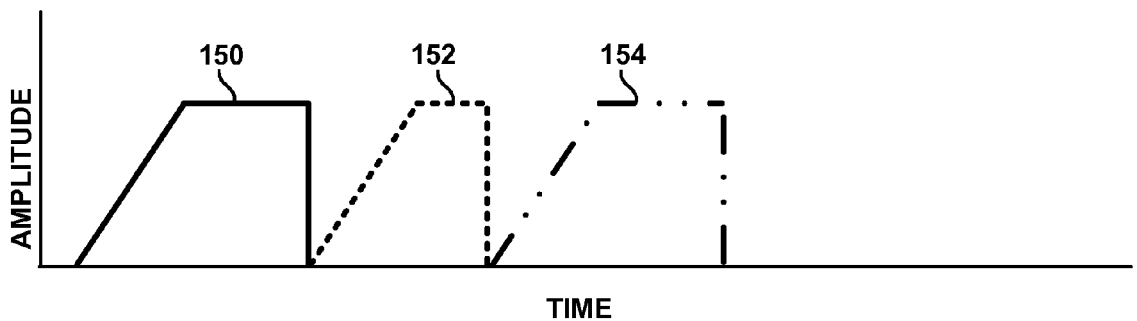
FIG. 15B is a graph illustrating another embodiment of discrete shifting of electrical stimulation between different electrode combinations.

FIG. 15B is a graph illustrating another embodiment of discrete shifting of electrical stimulation between different electrode combinations. In this embodiment, programmer 20 generates commands to cause stimulator 14 to immediately terminate stimulation completely to zero or some minimum level for an initial electrode combination before starting to ramp up stimulation amplitude for a shifted electrode combination. As shown in FIG. 15B, stimulation amplitude 150 for a first electrode combination is ramped up from zero to a target level by stimulator 14. In response to user input specifying a shift parameter adjustment, programmer 20 causes stimulator 14 to immediately decrease stimulation amplitude 150 for the first electrode combination down to zero.

Once zero or some minimum level is reached, programmer 20 causes stimulator 14 to ramp stimulation amplitude 152 up for a second electrode combination. Alternatively, stimulator 14 may automatically terminate and ramp up stimulation amplitude when a shift indication is received from programmer 20. Upon receipt of another shift parameter adjustment, programmer 20 causes stimulator 14 to immediately decrease stimulation amplitude 152 down to zero. Then, upon reaching zero or some minimum level, programmer 20 causes stimulator 14 to start (or stimulator 14 automatically starts) ramping up stimulation amplitude 154 on a third, shifted electrode combination. The process may continue in a similar manner for each newly shifted electrode combination.

Figure 16:
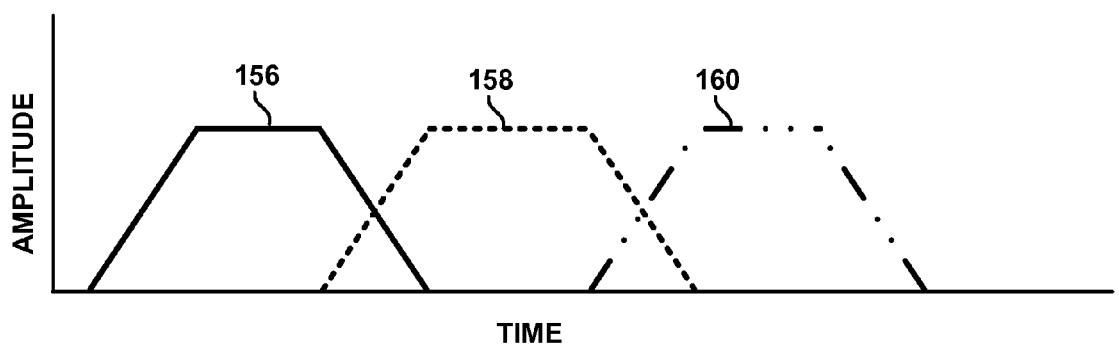
FIG. 16 is a graph illustrating overlapping shifting of electrical stimulation between different electrode combinations.

FIG. 16 is a graph illustrating overlapping shifting of electrical stimulation between different electrode combinations. The shifting shown in FIG. 16 generally conforms to FIG. 15, but illustrates overlapping of stimulation delivered to different electrode combinations. In the example of FIG. 16, in response to a shift parameter adjustment, programmer 20 causes stimulator to ramp down the amplitude 156 on a first electrode combination and simultaneously, for at least a portion of the ramp time, ramp up amplitude 158 on a second, shifted electrode combination. In other examples, amplitudes may only ramp one at a time. For examples, ramp up of amplitude 158 may be completed before ramp down of amplitude 156 is started.

The stimulation during the ramp time may be delivered simultaneously via both electrode combinations or on a time-interleaved basis in a series of incremental steps. For example, pulses or bursts of pulses may be delivered to the first electrode combination and second electrode combination in successive, alternating time slots to provide a perception of gradually shifting stimulation energy from one electrode combination to another. In each time slot, the amplitude of the pulse or burst may be gradually decreased for the initial electrode combination and gradually increased for the shifted electrode combination. A similar simultaneous or interleaved ramping may be applied to ramp down and ramp up stimulation amplitude 158 for the second electrode combination and stimulation amplitude 160 on the third electrode combination. The process may continue in a similar manner for each newly shifted electrode combination.

Example techniques for shifting stimulation between electrode combinations in an electrical stimulation device are described in commonly assigned U.S. Published Application No. 20060259099, to Goetz et al., the entire content of which is incorporated herein by reference. In some embodiments, such example techniques may be adapted to support shifting of stimulation among different electrode combinations using parameter-directed shifting techniques as described in this disclosure.

Some additional features may be desirable in an electrical stimulation system configured to support parameter-directed shifting of electrode combinations as described in this disclosure. As one example, it may be desirable to include a reset feature in programmer 20 to permit a patient to reset the electrode combination to an initial or original electrode combination after one or more shift operations. For example, by activating a single reset button, the user may be permitted to immediately return the stimulator 14 to an electrode combination that was in effect when the patient started the shifting process. With the reset feature, programmer 20 may return the stimulator 14 directly to an initial electrode combination. In this case, stimulator 14 may take several shift steps or directly access a particular electrode combination.

In some embodiments, programmer 20 may alternatively or additional include an undo feature, that permits a user to step backwards through shift step operations one at a time to return to a desired position, which may be the initial electrode combination or an intermediate electrode combination. Alternatively, the user may increment or decrement an applicable shift parameter value to achieve the same or similar effect. However, for simplicity and quick access, it may be desirable to provide a dedicated reset or undo button that is presented on a display of programmer 20 for selection by a patient or other user.

As an additional feature, a physician programmer is typically applied to support programming of stimulator 14. For example, a physician programmer may download multiple program groups, each containing one or more programs, and associated parameter settings for the programs, including stimulation amplitude, pulse width, pulse rate and electrode combination. To support parameter-directed shifting of electrode combinations, the physician programmer may be configured to designate selected groups as shiftable groups, or individual programs within a group as shiftable. For example, the physician programmer may provide a user interface that permits a physician or other user to designate different program groups as shiftable by simply checking a box or providing some other indication.

The physician programmer may download information to the stimulator or another programmer, such as a patient programmer, to indicate the shiftable status of different program groups and/or individual programs within such groups. When programmer 20 initiates the parameter-directed shifting process, it may refer to information transmitted to programmer 20 from the physician programmer or information stored in stimulator 14 and uploaded to programmer 20 to determine which programs or groups are shiftable. When a group or program is not shiftable, programmer 20 may be configured to prohibit presentation of the group or program as shiftable, e.g., by not presenting shift parameters corresponding to such a group or program. Likewise, a processor in stimulator 14 prohibits shifting if a program associated with one of the electrode combinations is indicated as not being shiftable, either directly or by not receiving a shift command from programmer 20.

When the programs are downloaded, either to the stimulator, a patient programmer, or both, they are flagged with the appropriate indication that they are either shiftable or not shiftable. In a similar manner, the physician programmer also may designate different parameters, such as amplitude, pulse width and pulse rate, as being adjustable by a user. In a consistent manner, a shift parameter value may be designated as adjustable or not adjustable to indicate whether shifting is available for programs in a group. In further embodiments, physician programmer may be configured to distinguish between different programs in a group. For example, an entire group may be designated as shiftable. Alternatively, selected programs in a group may be designated as shiftable, while some other programs in the same group are designated as non-shiftable.

As an additional feature, when adjusting the shift parameter value to cause a shift from one electrode combination to another for a given program in a group, programmer 20 may provide an optional mode to permit a global shift of electrode combinations for all programs within a group. As the programs in a group likely will vary in terms of the particular electrode combinations used to deliver stimulation, a set of rules may be provided to approximate similar shifts among electrode combinations associated with different programs.

A group shift lockout feature may be useful for patients with groups having programs characterized by high rates and pulse widths, and some shared electrodes among electrode combinations associated with the programs in the group. With higher rates and pulse widths, if a shift could cause two interleaved programs to share an electrode, it may be desirable to prohibit shifting for either the pertinent programs or the entire group of programs in which the pertinent programs reside, e.g., to avoid possible effects of charge build-up on an electrode shared by interleaved programs delivered in adjacent time slots. In this case, the pertinent programs or all programs in a group would be indicated as non-shiftable by a physician programmer. The physician programmer would then load the non-shiftable status into stimulator 14 for retrieval by programmer 20 or transmit the status directly to the programmer. If a group or program has the status of not shiftable, for the above reason or any other reason, programmer 20 may present a message indicating the status or simply present no options for the user to adjust a shift parameter value for the desire group or program.

As a further refinement or addition, in some embodiments, programmer 20 may present shift parameter values with textual names to indicate contexts or positions associated with shift positions. For example, instead of an arbitrary or ordered alphanumeric character, programmer 20 may present names to identify activities or positions with the electrode combination represented by the shift positions. In some embodiments, the patient may be permitted to select the names. For different positions or postures, for example, the user may specify different shift positions that provide desired efficacy for activities or posture such as sitting, standing, walking, lying down, morning, night, or the like. In some cases, different shift positions may be organized into groups that are named by a patient for different activities or postures.

Figure 17:
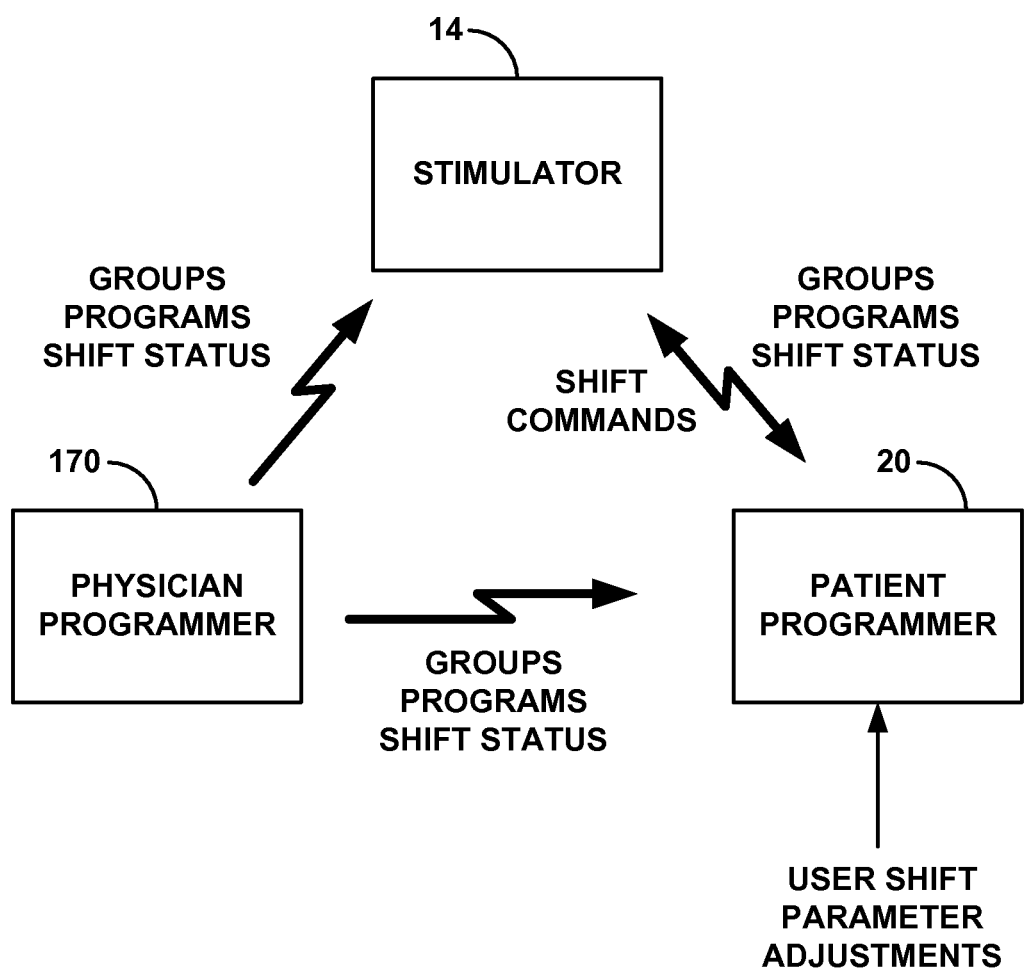
FIG. 17 is a block diagram illustrating exchange of shift status information among a physician programmer, stimulator and patient programmer.

FIG. 17 is a block diagram illustrating exchange of shift status information among a physician programmer 170, stimulator 14 and programmer 20. In the example of FIG. 17, programmer 20 is shown as a patient programmer. As shown in FIG. 17, physician programmer 170 may prepare and download to memory in stimulator 14 parameter sets associated with program groups, and programs within the groups, including applicable stimulation amplitudes, pulse widths, pulse rates, electrode combinations and polarities.

In addition, physician programmer 170 may download shift status information indicating whether a user of programmer 20, which may be a patient programmer, should be permitted to perform parameter-directed shifting with respect to a group or program. Some or all of such information may be additionally or alternatively transmitted or otherwise provided to patient programmer 20. In an exemplary embodiment, however, patient programmer 20 may upload information relating to groups, programs and shift status from stimulator 14, e.g., in its entirety or in portions when needed to support programming operations.

When parameter-directed shifting is initiated, for example, patient programmer 20 may retrieve shift status information from stimulator 14 and present appropriate shift parameter values to a user to permit parameter-directed shifting of electrode combinations for selected groups or programs. In response to user input indicating user shift parameter adjustments, patient programmer 20 transmits shift commands to stimulator 14 to cause the stimulator to perform the desired shifts of electrode combinations for the active program or programs. The information and commands may be transmitted by wireless telemetry or other media.

In general, if shift status indicates that a program is shiftable, programmer 20 may present a shift parameter value for the program. However, if the shift status indicates that a program is not shiftable, e.g., due to the possibility of electrode sharing among interleaved programs having high rates or pulse widths, programmer does not present a shift parameter value for the program. Instead, programmer 20 may present an indication that the program is not shiftable, e.g., as a visual or audible message, or simply not present a shift parameter value corresponding to the program. In this manner, programmer 20 may prohibit parameter adjustment if a particular electrode combination is indicated as not being shiftable. In particular, programmer 20 may cause the user interface associated with programmer 20 to prohibit adjustment of the shift parameter value if a particular electrode combination is indicated as not being shiftable in the shift status information.

Figure 18:
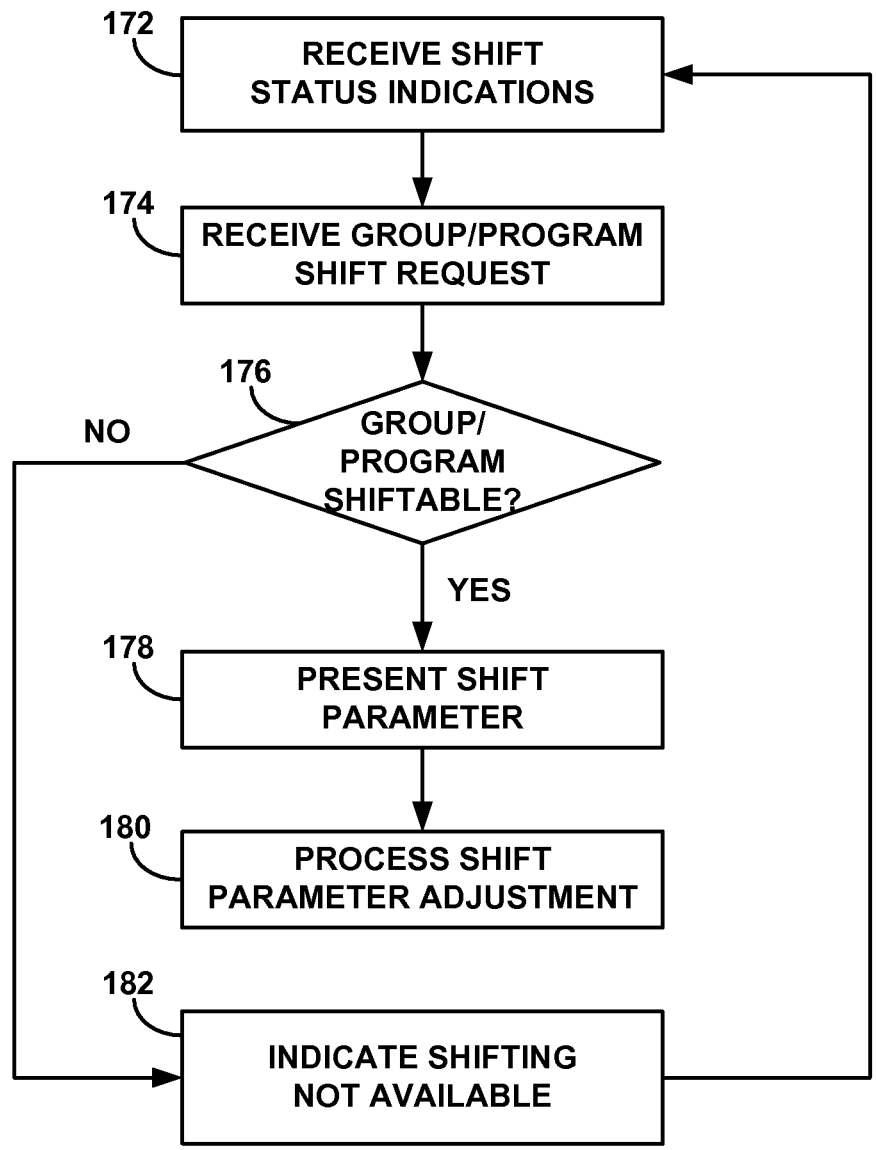
FIG. 18 is a flow diagram illustrating processing of shift status for different programs or groups.

FIG. 18 is a flow diagram illustrating processing of shift status for different programs or groups. As shown in FIG. 18, programmer 20 may receive shift status indications for particular groups and/or programs (172), e.g., directly from physician programmer 170 or by uploading the information from stimulator 14. Upon receiving a group or program shift request from a user (174), programmer 20 determines whether the group or program is indicated as being shiftable (176). Again, physician programmer 170 may restrict shifting of a particular group or program to avoid the possibility of shared electrodes among interleaved programs, or for other reasons.

If the group or program is shiftable, programmer 20 presents a pertinent shift parameter, e.g., 1/3, 3/4, or the like, for the desired group or program (178). Programmer 20 then processes any shift parameter adjustments made by the user (180) and sends corresponding shift commands to stimulator 14. If the group or program is not shiftable (176), programmer 20 indicates that shifting is not available (182), e.g., by presenting an explicit message to that effect or simply not presenting a pertinent shift parameter value for the desired group or program. Hence, programmer 20 prohibits parameter adjustment if a program associated with the first electrode combination is indicated as not being shiftable.

This disclosure describes techniques for shifting electrode combinations. The techniques may be adapted for axial shifting of electrode combinations along the length of one or more electrode arrays, such as along the length extending between proximal and distal ends of one or more leads. The disclosure provides various examples of axial shifting. In some examples, reference to a vertical orientation is for purposes of convenience, as leads or other electrode arrays may assume any of a variety of orientations depending on the actual orientation at which the lead or array is implanted relative to a target stimulation site. Accordingly, even though the term "vertical" may be used as a convenient term of reference for axial movement along the length of a lead between proximal and distal ends, the actual orientation may be vertical, horizontal, or oblique relative to the patient or the earth. For example, when a patient is standing up, leads implanted adjacent the spinal cord may in fact be vertical, and may be considered vertical regardless of posture relative to the patient's body length. In other examples, however, a deep brain lead, sacral lead or pudendal lead may occupy a different orientation relative to the patient's body length.

In addition, the shifting techniques may be adapted for lateral shifting of electrode combinations among two or more adjacent electrode arrays, such as two or more adjacent implantable leads. Hence, the shift from the first electrode combination to the second electrode combination may be axial along a length of one or more adjacent leads, or lateral across a set of two or more adjacent leads. In each case, the shift may be indicated by a shift parameter value adjustment. In some embodiments, a first shift parameter may be provided for axial shifting and a second shift parameter may be provided for lateral shifting. In other embodiments, different values of a single shift parameter may be used to indicate different combinations of axial and lateral shifting such that a given shift parameter value indicates an electrode combination associated with a lateral and axial position within a grid.

The adjacent implantable leads may have longitudinal axes that are substantially parallel to one another. For example, if there are three leads and an electrode combination includes electrodes on a first (e.g., left) and second (middle) lead, but not a third (e.g., right) lead, the electrode combination could be shifted from left to right such that the electrodes on the first lead are shifted to corresponding electrodes on the second lead and the electrodes on the second lead are shifted to corresponding electrodes on the third lead. Similarly, an electrode combination could be shifted from right to left if the electrode combination were formed by electrodes on the second and third leads. In each case, the shift could be performed in response to parameter-directed shift input from a user of programmer 20. In particular, each lateral shift (right to left or left to right) may be represented by a lateral shift parameter value. In general, parameter-directed lateral shifting techniques as described in this disclosure may apply to any number of adjacent implantable leads, such as two, three, four, five or more leads. In addition, such leads may include the same electrode counts or different electrode counts.

When the user, such as a patient, adjusts the shift parameter value (e.g., 1/3, 2/3, etc.), programmer 20 may cause stimulator 14 to deliver stimulation via a laterally shifted electrode combination that corresponds to the resulting shift parameter value. As in the case of axial shifting, the number of shift possibilities may be determined in relation to maximum left and right boundaries, limiting the number of shift parameter values and associated electrode combinations. Also, shift possibilities and associated shift parameter values may be determined in part by the shapes of the electrode combination. For example, if there are three leads, and a program specifies an electrode combination that includes electrodes only on one of the leads, e.g., the left lead, then there are three different shift possibilities, i.e., left lead (1/3), middle lead (2/3) and right lead (3/3). If there are three leads, and a program specifies an electrode combination that includes electrodes on two leads, e.g., left and middle, then there may be only two possibilities, left and middle (1/2) and middle and right (1/3). As a further alternative, electrode combinations may be rotated among the leads, creating additional possibilities, as described in further detail below.

If a user attempts to shift beyond a boundary, programmer 20 may advise the user that the shift is not possible, or simply not present the desired shift as one of the options in terms of available shift parameter values. As an alternative, the shift parameter values may wrap around such that a right-ward shift of the last combination on the right results in the first combination on the left, and a left-ward shift of the last combination on the left results in the first combination on the right. For example, if combinations are numbered 1/3, 2/3, 3/3 from left to right, then a left-ward shift of the 1/3 combination may result in the 3/3 combination. Similarly, a right-ward shift of the 3/3 combination may result in the 1/3 combination. This rotating, wrap-around shifting process may be useful in any lead configuration, and particularly useful for implant configurations in which three or more laterally adjacent leads do not necessarily reside in the same plane, but instead are arranged to form an arc around a tissue stimulation site such as the spinal cord.

For a rotational shifting technique that permits wrap-around from right to left and from left to right, an electrode combination may have additional shift possibilities. As an illustration, it is assumed the lead configuration includes three leads (0, 1 and 2) with four electrodes each (0, 1, 2, 3 from distal to proximal). For an electrode combination of (2/0, 1/1, 2/1), with a rotational shifting technique, there may be the following shift possibilities: (2/0, 1/1, 2/1); (2/1, 1/2, 2/2), (2/2, 1/0, 2/0). Similarly, with three leads, for an electrode combination of (2/0, 1/1, 2/1, 2/2), there are the following shift possibilities: (2/0, 1/1, 2/1, 2/2), (2/1, 1/2, 2/2, 2/0), (2/2, 1/0, 2/0, 2/1). In general, each of the lateral shift possibilities for bounded shifting or rotational shifting may be selected by adjusting or selecting a shift parameter value via the user interface of a programmer 20 in the ways described in this disclosure for axial ("vertical") shifting. In addition, similar features such as global group shifting and imposition of shifting restrictions or prohibitions by a physician programmer, stimulator or patient programmer can be applied to lateral shifting.

Axial and lateral shifting may be provided, e.g., on a parameter-directed basis, for electrode combinations formed by combinations of electrodes in one, two or more adjacent electrode arrays. Each electrode array may be formed by electrodes on one or more implantable leads. For example, adjacent leads may include an axial array of electrodes extending from a most-proximal electrode to a most-distal electrode. Alternatively, at least some of the electrode arrays may be formed by rows and/or columns of electrodes arranged on a surface of a stimulator housing, or on a paddle lead. A paddle lead, for example, may include multiple rows and columns of electrodes. Lateral and/or vertical shifting among different electrode combinations formed by electrodes in rows and/or columns on a single paddle lead or multiple paddle leads. Hence, a shift may traverse rows and/or columns within a single paddle lead or extend across multiple paddle leads.

Accordingly, a shift from a first electrode combination to a second electrode combination may be axial along a length of one or more adjacent leads, or axial along the length of one or more columns on a single lead. Also, a shift from a first electrode combination to a second electrode combination may be lateral across a set of two or more adjacent leads, or lateral across columns of electrodes on a single lead. As a further alternative, a shift from a first electrode combination to a second electrode combination may be both axial along a length of one or more adjacent leads, or axial along the length of one or more columns on a single lead, and lateral across a set of two or more adjacent leads, or lateral across columns of electrodes on a single lead. In other words, in some embodiments, a shift may have both axial and lateral components, which may effectively result in diagonal shifting. In each case, the pertinent axial, lateral, or axial/lateral shift may be associated with a particular shift parameter value.

Although the present disclosure has described various embodiments for parameter-directed shifting of electrical stimulation among different electrode combinations that may have substantially similar electrode patterns for an implantable stimulation device, it is also contemplated that such electrode combinations may also be utilized and shifted in external stimulation devices as well, according to some embodiments. Thus, the techniques described in this disclosure may be implemented in one or more external programming devices, external stimulation devices, and/or implantable stimulation devices.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Many embodiments of the invention have been described. Various modifications may be made without departing from the scope of the claims. These and other embodiments are within the scope of the following claims.

The invention claimed is:

1. A method comprising:
delivering electrical stimulation via an electrode combination comprising at least one active electrode in a first array of electrodes and at least one active electrode in a second array of electrodes, wherein the second array includes a greater number of electrodes than the first array, wherein each electrode of the first array is positioned at a respective level within the first array, and wherein each electrode of the second array is positioned at a respective level within the second array; and
shifting the electrical stimulation to different electrode combinations in a series of shift operations, wherein one of the shift operations includes shifting a position of all active electrodes in the second array while maintaining a position of all active electrodes in the first array, and wherein shifting the position of all active electrodes in the second array comprises performing a single level shift of the position of all active electrodes in the second array.

2. The method of claim 1, wherein the electrode combination further comprises at least one active electrode in a third array of electrodes, wherein the third array and the first array include a common number of electrodes, and wherein one of the shift operations includes shifting the position of all the active electrodes in the second array while maintaining the position of all the active electrodes in the first array and maintaining a position of all the active electrodes in the third array.

3. The method of claim 2, wherein the first array consists of four electrodes, the second array consists of eight electrodes, and the third array consists of four electrodes.

4. The method of claim 1, wherein the one of the shift operations comprises a first shift operation, and wherein the series of shift operations comprises a second shift operation that includes shifting the position of all the active electrodes in the second array and shifting the position of all the active electrodes in the first array.

5. The method of claim 4, further comprising, on a substantially alternating basis, shifting the position of all the active electrodes in the second array while maintaining the position of all the active electrodes in the first array, and shifting the positions of both all the active electrodes in the second array and all the active electrodes in the first array.

6. The method of claim 4, wherein shifting includes shifting the electrical stimulation in one of a first direction and a second direction based on user input.

7. The method of claim 6, further comprising shifting the position of all the active electrodes in the second array while maintaining the position of all the active electrodes in the first array when the shifting is in the first direction and all the active electrodes in the second array is at an odd-numbered position within the second array.

8. The method of claim 6, further comprising shifting the position of all the active electrodes in the second array and shifting the position of all the active electrodes in the first array when the shifting is in the first direction and the most proximal of the active electrodes in the second array is at an even-numbered position within the second array.

9. The method of claim 6, further comprising shifting the position of all the active electrodes in the second array while maintaining the position of all the active electrodes in the first array when the shifting is in the second direction and the most proximal active electrode in the second array is at an even-numbered position within the second array.

10. The method of claim 6, further comprising shifting the position of all the active electrodes in the second array and shifting the position of all the active electrodes in the first array when the shifting is in the second direction and the most proximal active electrode in the second array is at an odd-numbered position within the second array.

11. The method of claim 1, wherein the first array consists of four electrodes and the second array consists of eight electrodes.

12. The method of claim 1, wherein the first array of electrodes is arranged on a first implantable lead, and the second array of electrodes is arranged on a second implantable lead.

13. The method of claim 12, wherein the first and second implantable leads are coupled to a stimulation pulse generator.

14. The method of claim 1, further comprising shifting the electrical stimulation in response to one or more shift commands received from a programmer.

15. The method of claim 1, further comprising shifting the electrical stimulation for multiple programs within a group of programs.

16. The method of claim 1, wherein the electrode combination includes multiple electrodes in at least one of the first and second arrays.

17. The method of claim 1, further comprising shifting the electrical stimulation in response to user input indicating a parameter adjustment that indicates the shift operations to different electrode combinations.

18. The method of claim 1, further comprising prohibiting shifting if a program associated with one of the electrode combinations is indicated as not being shiftable.

19. The method of claim 1, wherein delivering the electrical stimulation comprises delivering one of spinal cord stimulation, pelvic floor stimulation, gastric stimulation, brain stimulation, or peripheral nerve stimulation.

20. The method of claim 1, wherein delivering electrical stimulation via the electrode combination comprises delivering voltage-based or current-based stimulation.

21. An electrical stimulation device comprising:
a first array of electrodes, wherein each electrode of the first array is positioned at a respective level within the first array;
a second array of electrodes including a greater number of electrodes than the first array of electrodes, wherein each electrode of the second array is positioned at a respective level within the second array;
an electrical stimulation generator that generates electrical stimulation and delivers the electrical stimulation via an electrode combination comprising at least one active electrode in the first array and at least one active electrode in a second array; and
a processor that controls the electrical stimulation generator to shift the electrical stimulation to different electrode combinations in a series of shift operations, wherein one of the shift operations includes shifting a position of the all active electrodes in the second array while maintaining a position of all the active electrodes in the first array, and wherein shifting the position of all the active electrodes in the second array comprises performing a single level shift of the position of all the active electrodes in the second array.

22. The device of claim 21, further comprising a third array of electrodes, wherein the third array and the first array include a common number of electrodes, wherein the electrode combination further comprises an active electrode in the third array, and wherein one of the shift operations includes shifting the position of all the active electrodes in the second array while maintaining the position of all the active electrodes in the first array and maintaining a position of all the active electrodes in the third array.

23. The device of claim 22, wherein the first array consists of four electrodes, the second array consists of eight electrodes, and the third array consists of four electrodes.

24. The device of claim 21, wherein the one of the shift operations comprises a first shift operation, and wherein the series of shift operations comprises a second shift operation that includes shifting the position of all the active electrodes in the second array and shifting the position of all the active electrodes in the first array.

25. The device of claim 24, wherein the processor controls the electrical stimulation generator to, on a substantially alternating basis, shift the position of all the active electrodes in the second array while maintaining the position of all the active electrodes in the first array and shift the positions of both all the active electrodes in the second array and all the active electrodes in the first array.

26. The device of claim 24, wherein the processor controls the electrical stimulation generator to shift the electrical stimulation in one of a first direction and a second direction based on user input.

27. The device of claim 26, wherein the processor controls the electrical stimulation generator to shift the position of all the active electrodes in the second array while maintaining the position of all the active electrodes in the first array when the shifting is in the first direction and the most proximal active electrode in the second array is at an odd-numbered position within the second array.

28. The device of claim 26, wherein the processor controls the electrical stimulation generator to shift the position of all the active electrodes in the second array and shift the position of all the active electrodes in the first array when the shifting is in the first direction and the most proximal active electrode in the second array is at an even-numbered position within the second array.

29. The device of claim 26, wherein the processor controls the electrical stimulation generator to shift the position of all the active electrodes in the second array while maintaining the position of all the active electrodes in the first array when the shifting is in the second direction and the most proximal active electrode in the second array is at an even-numbered position within the second array.

30. The device of claim 26, wherein the processor controls the electrical stimulation generator to shift the position of all the active electrodes in the second array and shift the position of all the active electrodes in the first array when the shifting is in the second direction and the most proximal active electrode in the second array is at an odd-numbered position within the second array.

31. The device of claim 21, wherein the first array consists of four electrodes and the second array consists of eight electrodes.

32. The device of claim 21, further comprising a first implantable lead coupled to the stimulation generator and carrying the first array of electrodes and a second implantable lead coupled to the stimulation generator and carrying the second array of electrodes.

33. The device of claim 21, wherein the processor controls the electrical stimulation generator to shift the electrical stimulation in response to one or more shift commands received from a programmer.

34. The device of claim 21, wherein the processor controls the electrical stimulation generator to shift the electrical stimulation for multiple programs within a group of programs.

35. The device of claim 21, wherein the electrode combination includes multiple electrodes in at least one of the first and second arrays.

36. The device of claim 21, wherein the processor causes the electrical stimulation generator to shift the electrical stimulation based on user input indicating a parameter adjustment that indicates the shift operations to different electrode combinations.

37. The device of claim 21, wherein the processor prohibits shifting if a program associated with one of the electrode combinations is indicated as not being shiftable.

38. The device of claim 21, wherein the electrical stimulation generator that delivers the electrical stimulation via the electrode combination delivers one of spinal cord stimulation, pelvic floor stimulation, gastric stimulation, brain stimulation, or peripheral nerve stimulation.

39. The device of claim 21, wherein the electrical stimulation comprises voltage-based or current-based stimulation.

40. An electrical stimulator system comprising:
an electrical stimulator that delivers electrical stimulation via an electrode combination comprising at least one active electrode in a first array of electrodes and at least one active electrode in a second array of electrodes, wherein the second array includes a greater number of electrodes than the first array, wherein each electrode of the first array is positioned at a respective level within the first array, and wherein each electrode of the second array is positioned at a respective level within the second array; and
an external programmer that controls the electrical stimulator to shift the electrical stimulation to different electrode combinations in a series of shift operations, wherein one of the shift operations includes shifting a position of all the active electrodes in the second array while maintaining a position of all the active electrodes in the first array, and wherein shifting the position of all the active electrodes in the second array comprises performing a single level shift of all the active electrodes in the second array.

41. The system of claim 40, wherein the electrode combination further comprises at least one active electrode in a third array, wherein the third array and the first array include a common number of electrodes, and wherein one of the shift operations includes shifting the position of all the active electrodes in the second array while maintaining the position of all the active electrodes in the first array and maintaining a position of all the active electrodes in the third array.

42. The system of claim 41, wherein the first array consists of four electrodes, the second array consists of eight electrodes, and the third array consists of four electrodes.

43. The system of claim 40, wherein the external programmer includes a user interface that receives user input indicating one or more of the shift operations, and a processor that generates commands to control the electrical stimulator based on the user input.

44. The system of claim 40, wherein the one of the shift operations comprises a first shift operation, and wherein the series of shift operations comprises a second shift operation that includes shifting the position of all the active electrodes in the second array and shifting the position of all the active electrodes in the first array.

45. The system of claim 44, wherein the programmer controls the electrical stimulator to, on a substantially alternating basis, shift the position of all the active electrodes in the second array while maintaining the position of all the active electrodes in the first array and shift the positions of both all the active electrodes in the second array and all the active electrodes in the first array.

46. The system of claim 44, wherein the programmer controls the electrical stimulator to shift the electrical stimulation in one of a first direction and a second direction based on user input.

47. The system of claim 46, wherein the programmer controls the electrical stimulator to shift the position of all the active electrodes in the second array while maintaining the position of all the active electrodes in the first array when the shifting is in the first direction and the most proximal active electrode in the second array is at an odd-numbered position within the second array.

48. The system of claim 46, wherein the programmer controls the electrical stimulator to shift the position of all the active electrodes in the second array and shift the position of all the active electrode in the first array when the shifting is in the first direction and the most proximal active electrode in the second array is at an even-numbered position within the second array.

49. The system of claim 46, wherein the programmer controls the electrical stimulator to shift the position of all the active electrodes in the second array while maintaining the position of all the active electrodes in the first array when the shifting is in the second direction and the most proximal active electrode in the second array is at an even-numbered position within the second array.

50. The system of claim 46, wherein the programmer controls the electrical stimulator to shift the position of all the active electrodes in the second array and shift the position of all the active electrodes in the first array when the shifting is in the second direction and the most proximal active electrode in the second array is at an odd-numbered position within the second array.

51. The system of claim 40, wherein the first array consists of four electrodes and the second array consists of eight electrodes.

52. The system of claim 40, further comprising a first implantable lead coupled to the stimulator and carrying the first array of electrodes and a second implantable lead coupled to the stimulator and carrying the second array of electrodes.

53. The system of claim 40, wherein the programmer controls the electrical stimulator to shift the electrical stimulation in response to one or more shift commands received from a programmer.

54. The system of claim 40, wherein the programmer controls the electrical stimulator to shift the electrical stimulation for multiple programs within a group of programs.

55. The system of claim 40, wherein the electrode combination includes multiple electrodes in at least one of the first and second arrays.

56. The system of claim 40, wherein the processor causes the electrical stimulation generator to shift the electrical stimulation based on user input indicating a parameter adjustment that indicates the shift operations to different electrode combinations.

57. The system of claim 40, wherein the processor prohibits shifting if a program associated with one of the electrode combinations is indicated as not being shiftable.

58. The system of claim 40, wherein the electrical stimulator that delivers electrical stimulation via the electrode combination delivers one of spinal cord stimulation, pelvic floor stimulation, gastric stimulation, brain stimulation, or peripheral nerve stimulation.

59. The system of claim 40, wherein the electrical stimulation comprises voltage-based or current-based stimulation.

60. An electrical stimulation device comprising:
means for delivering electrical stimulation via an electrode combination comprising an active electrode in a first array of electrodes and an active electrode in a second array of electrodes, wherein the second array includes a greater number of electrodes than the first array, wherein each electrode of the first array is positioned at a respective level within the first array, and wherein each electrode of the second array is positioned at a respective level within the second array; and
means for shifting the electrical stimulation to different electrode combinations in a series of shift operations, wherein one of the shift operations includes shifting a position of all the active electrodes in the second array while maintaining a position of all the active electrodes in the first array, and wherein shifting the position of all the active electrodes in the second array comprises performing a single level shift of all the active electrodes in the second array.

* * * * *